US007270997B2

(12) United States Patent
Ramsingh et al.

(10) Patent No.: US 7,270,997 B2
(45) Date of Patent: Sep. 18, 2007

(54) COXSACKIEVIRUS B4 EXPRESSION VECTORS AND USES THEREOF

(76) Inventors: Arlene I. Ramsingh, 34 Placid La., Glenmont, NY (US) 12077; Sadia S. Halim, 82 Beaver St., #1009, New York, NY (US) 10005

( * ) Notice: Subject to any disclaimer, the term of this patent is extended or adjusted under 35 U.S.C. 154(b) by 336 days.

(21) Appl. No.: 09/879,572

(22) Filed: Jun. 12, 2001

(65) Prior Publication Data

US 2002/0197711 A1 Dec. 26, 2002

(51) Int. Cl.
*C12N 15/00* (2006.01)
(52) U.S. Cl. .................. 435/320.1; 536/23.1
(58) Field of Classification Search ............. 435/320.1; 536/23.4, 23.1
See application file for complete search history.

(56) References Cited

U.S. PATENT DOCUMENTS 6,323,024 B1 * 11/2001 Tracy et al. ............. 435/320.1

FOREIGN PATENT DOCUMENTS

WO WO98/39426 * 9/1998

OTHER PUBLICATIONS

Saag et al., "HIV-1 and HAART: A Time to Cure, a Time to Kill," Nature Medicine, Jun. 1999, vol. 5, No. 6, pp. 609-611.
Gotch et al., "Therapeutic Vaccines in HIV.1 Infection," Immunological Reviews, 1999, vol. 170, pp. 173-182.
Rueckert, R. R., "Picornaviridae: The Viruses and Their Replication," *Fundamental Virology*, 3rd ed. Philadelphia: Lippincott-Raven, 1996, Chapter 16, pp. 477-522.
Melnick, J. L., "Enteroviruses: Polioviruses, Coxsackieviruses, Echoviruses, and Newer Enteroviruses," *Fields Virology*. In: Fields, B. N., Knipe, D. M., Howley, P. M., et al. editors. 3rd ed. Philadelphia: Lippincott—Raven Publishers, 1996, Chapter 22, pp. 655-712.
Jenkins et al., "The Complete Nucleotide Sequence of Coxsackievirus B4 and Its Comparison to Other Members of the Picornaviridae," Journal of General Virology, 1987, vol. 68, pp. 1835-1848.
Halim et al., "A Point Mutation in VP1 of Coxsackievirus B4 Alters Antigenicity," Virology, 2000, vol. 269, pp. 86-94.
Dedieu et al., "Poliovirus Chimeras Expressing Sequences from the Principal Neutralization Domain of Human Immunodeficiency Virus Type I," Journal of Virology, May 1992, vol. 66, No. 5, pp. 3161-3167.
Evans et al., "An Engineered Poliovirus Chimaera Elicits Broadly Reactive HIV-1 Neutralizing Antibodies," Nature, Jun. 1989, vol. 339, pp. 385-388.
Jenkins et al., "An Antigen Chimera of Poliovirus Induces Antibodies Against Human Papillomavirus Type 16," Journal of Virology, Mar. 1990, vol. 64, pp. 1201-1206.
Murdin et al., "A Poliovirus Hybrid Expressing a Neutralization Epitope from the Major Outer Membrane Protein of *Chlamydia trachomatis* is Highly Immunogenic," Infection and Immunity, Oct. 1993, vol. 61, No. 10, pp. 4406-4414.
Lu et al., "Construction and Genetic Analysis of Dicistronic Polioviruses Containing Open Reading Frames for Epitopes of Human Immunodeficiency Virus Type 1 gp120," Journal of Virology, Aug. 1995, vol. 69, No. 8, pp. 4797-4806.
Andino et al., "Engineering Poliovirus as a Vaccine Vector for the Expression of Diverse Antigens," Science, Sep. 1994, vol. 265, pp. 1448-1451.
Mueller et al., "Expression of Foreign Proteins by Poliovirus Polyprotein Fusion: Analysis of Genetic Stability Reveals Rapid Deletions and Formation of Cardioviruslike Open Reading Frames," Journal of Virology, Jan. 1998, vol. 72, No. 1, pp. 20-31.
Tang et al., "Toward a Poliovirus-Based Simian Immunodeficiency Virus Vaccine: Correlation Between Genetic Stability and Immunogenicity," Journal of Virology, Oct. 1997, vol. 71, pp. 7841-7850.
Ramsingh et al., "Severity of Disease Induced by a Pancreatropic Coxsackie B4 Virus Correlates with the H-2Kq Locus of the Major Histocompatibility Complex," Virus Research, 1989, vol. 14, pp. 347-358.
Caggana et al., "Identification of a Single Amino Acid Residue in the Capsid Protein VP1 of Coxsackievirus B4 That Determines the Virulent Phenotype," Journal of Virology, Aug. 1993, vol. 67, No. 8, pp. 4797-4803.
Ramsingh et al., "Differential Recruitment of B and T Cells in Coxsackievirus B4-Induced Pancreatitis is Influenced by a Capsid Protein," Journal of Virology, Nov. 1997, vol. 71, No. 11, pp. 8690-8697.
Ramsingh et al., "Identification of Candidate Sequences that Determine Virulence in Coxsackievirus B4," Virus Research, 1992, vol. 23, pp. 281-292.
Ramsingh et al., "A Point Mutation in the VP4 Coding Sequence of Coxsackievirus B4 Influences Virulence," Journal of Virology, Nov. 1995, vol. 69, No. 11, pp. 7278-7281.
Hofling et al., "Expression of an Antigenic Adenovirus Epitope in a Group B Coxsackievirus," Journal of Virology, May 2000, vol. 74, No. 10, pp. 4570-4578.

(Continued)

*Primary Examiner*—Stacy B. Chen
(74) *Attorney, Agent, or Firm*—Browdy and Neimark PLLC

(57) ABSTRACT

Disclosed is a recombinant attenuated coxsackievirus B4 virion which is engineered to contain a heterologous nucleic acid within the open reading frame of its genome, wherein the heterologous nucleic acid encodes a heterologous polypeptide which is expressed by the virion. Specific examples of attenuated coxsackievirus B4 virions suitable for use in the present invention are CB4-P and JVB. In one embodiment the heterologous nucleic acid is inserted into the P1 region of the genome such that the heterologous polypeptide is expressed as a fusion of a viral capsid protein. Methods of use of the recombinant attenuated coxsackievirus B4 virion include inducing an immune response in an individual to the heterologous polypeptide contained therein.

46 Claims, 14 Drawing Sheets

OTHER PUBLICATIONS

M. A. Pallansch, "Coxsackievirus B Epidemiology and Public Health Concerns," Current Topics Microbiol Immunol, 1997, vol. 223, pp. 13-30.

Rosenberg et al., "Vigorous HIV-1-Specific CD4+ T Cell Responses Associated with Control of Viremia," Science, Nov. 1997, vol. 278, pp. 1447-1450.

Ramsingh et al., "Coxsackieviruses and Diabetes," BioEssays, 1997, vol. 19, No. 9, pp. 793-800.

Muckelbauer et al., "The Structure of Coxsackievirus B3 at 3.5 A Resolution," Structure, Jul. 1995, vol. 3, No. 7, pp. 653-667.

Murphy et al., "Induction by Antigen of Intrathymic Apoptosis of CD4+ CD8+ TCRlo Thymocytes in Vivo," Science Dec. 1990, vol. 250, pp. 1720-1722.

Ramsingh et al., "T Cells Contribute to Disease Severity During Coxsackievirus B4 Infection," Journal of Virology, Apr. 1999, vol. 73, No. 4, pp. 3080-3086.

Hunt et al., "Peptides Presented to the Immune System by the Murine Class II Major Histocompatibility Complex Molecule I-Ad," Science, Jun. 1992, vol. 256, pp. 1817-1820.

Coligan et al., "Chapter 2—Antibody Detection and Preparation," pp. 2.0.1-2.1.6 and Chapter 3—"In Vitro Assays for Mouse Lymphocyte Function," pp. 3.0.1-3.12.14, *Current Protocols in Immunology*. New York: JohnWiley & Sons, 1996.

Janeway et al., "Chapter 4—Antigen Recognition by T Lymphocytes," pp. 4:1-4:21, Immunobiology: The Immune System in Health and Disease. 3rd ed. London, NewYork: Current Biology Ltd./Garland Publishing Inc., 1997.

Halim et al., "Immunogenicity of a Foreign Peptide Expressed Within a Capsid Protein of an Attenuated Coxsackievirus," Vaccine, 2001, vol. 19, pp. 958-965.

Chapman et al., "Genetics of Coxsackievirus Virulence," Current Topics Microbiol Immunol, 1997, vol. 223, pp. 227-258.

Killeen et al., "Regulated Expression of Human CD4 Rescues Helper T Cell Development in Mice Lacking Expression of Endogenous CD4," EMBO J, 1993, vol. 12, pp. 1547-1553.

Noben-Trauth et al., "Susceptibility to Leishmania Major Infection in Interleukin-4-Deficient Mice," Science, Feb. 1996, vol. 271, pp. 987-990.

Dalton et al., "Multiple Defects of Immune Cell Function in Mice with Disrupted Interferon-Gamma Genes," Science, Mar. 1993, vol. 259, pp. 1739-1742.

Henderson et al., "Gag Proteins of the Highly Replicative MN Strain of Human Immunodeficiency Virus Type 1: Posttranslational Modifications, Proteolytic Processings, and Complete Amino Acid Sequences," Journal of Virology, Apr. 1992, vol. 66, No. 4, pp. 1856-1865.

Page et al., "Construction and Use of a Human Immunodeficiency Virus Vector for Analysis of Virus Infectivity," Journal of Virology, Nov. 1990, vol. 64, pp. 5270-5276.

Halim et al., "A Therapeutic HIV Vaccine Using Coxsackie-HIV Recombinants: A Possible New Strategy," Aids Research and Human Retroviruses, 2000, vol. 16, No. 15, pp. 1551-1558.

* cited by examiner

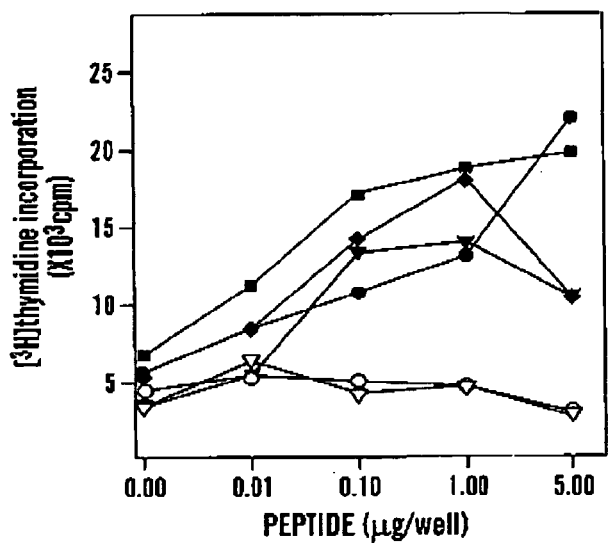 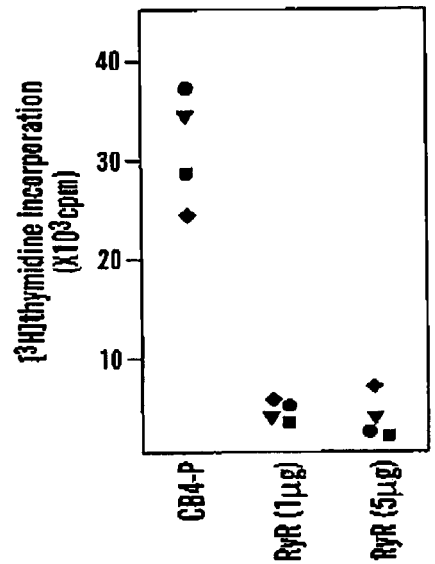
*FIG. 1A*  *FIG. 1B*
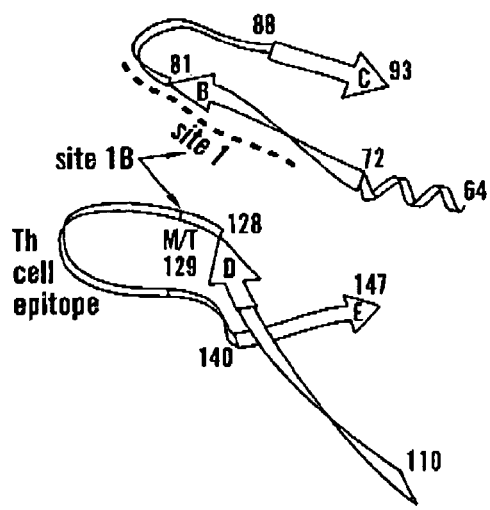
*FIG. 1C*

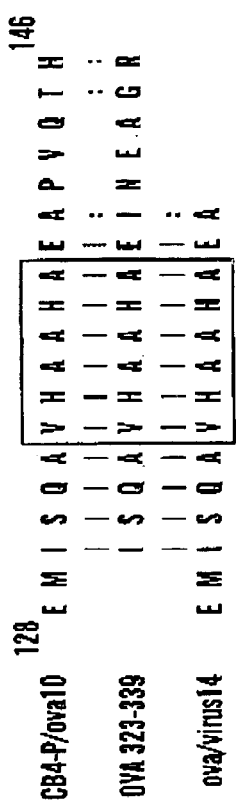
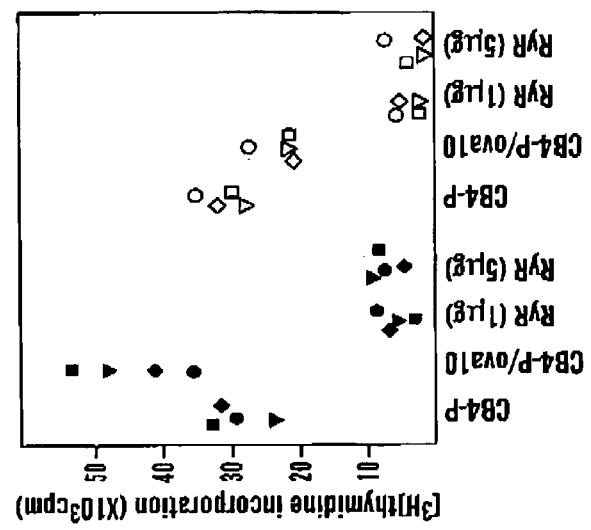
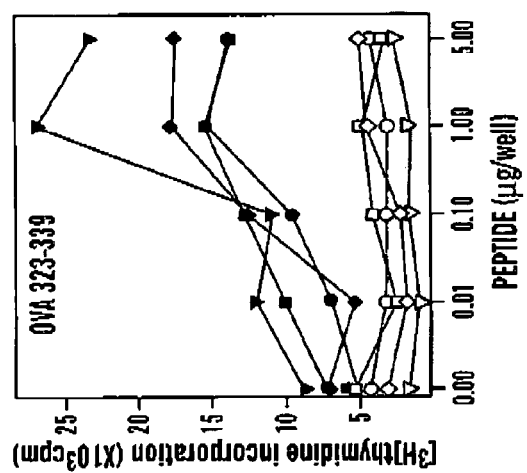
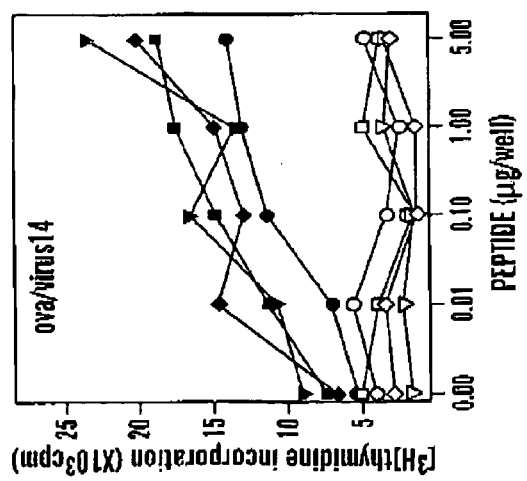
FIG. 5A
FIG. 5B
FIG. 5C
FIG. 5D

```
              2826
CB4-P/HIV1074       CAGGAGATGAAGAGGAAGCTGCAGAATGGGATAGACTAGGGGCCGCCAGTGCAG
CB4-P/HIV9104       ....-..ATAGCAGAACTAGTAGTACCCTTCAG---..-.-..-..-.
CB4-P/BIV9198       ....-..AGCAGCATTCTGACACATAAGACAAGGA---..-.-..-..-.
```

FIG. 8

```
                         p24
              M   t   r   g   h   q   a   a   m   q   m   l   k    782
   735  TACGATAAAATGACGCGTGGACATCAAGCAGCCATGCAAATGTTAAAA....
CB4-P/HIV62
CB4-P/HIV35   ..............................................

e   t   i   n   e   e   a   a   e   w   d   r   v   h   p   v    829

COXSACKIEVIRUS B4 EXPRESSION VECTORS AND USES THEREOF

GOVERNMENT SUPPORT

This work was supported in part by grant number DK43929 from the National Institute of Health.

RELATED APPLICATIONS

Each of the patent applications, patents, and other publications cited in this text, are hereby expressly incorporated herein by reference.

BACKGROUND OF THE INVENTION

An ultimate goal in the treatment of HIV-infected persons is to prevent disease progression. Therapeutic HIV vaccines have been developed to protect HIV-infected individuals from progression to AIDS. Current HIV vaccines include Remune, an inactivated HIV-1 lacking the gp120 glycoprotein, VaxSyn, a recombinant gp160, and p24 virus-like particles. Another approach in the treatment of HIV-infected persons is to use chemotherapy to reduce viral load, followed by immunotherapy to stimulate desirable HIV-specific immune responses, such as those observed among long-term asymptomatic HIV-infected individuals.

During the past ten years, chemotherapy for HIV-infected individuals has advanced rapidly. Current treatment consists of a cocktail of anti-retroviral drugs termed highly active anti-retroviral therapy (HAART). While HAART reduces viral load, it does not eradicate HIV (Saag and Kilby, *Nature Medicine* 5(6): 609-11 (1999)). In addition, HAART is often associated with drug-related toxicity and the selection of drug-resistant mutants. Additional strategies would therefore be desirable to treat HIV-infected individuals.

A body of work suggests that continued health maintenance in patients with long-term non-progressive HIV infection can be attributed to effective CTL responses in general, and gag-specific CTL responses in particular, each driven by vigorous antigen-specific CD4+ T helper cells (Gotch et al., *Immunol. Rev.*: 170173-82 (1999)). Thus, one strategy in the treatment of HIV-infected individuals involves the reduction of viral load with HAART, followed by modulation of the host's immune response such that it mimics the protective immunogenic response found among long-term asymptomatic HIV-infected patients (Gotch et al., *Immunol. Rev.*: 170173-82 (1999)).

Modulation of the host's immune response can be carried out with the use of a viral vaccine which induces in the host both CTL and CD4+ T helper cell responses. Thus, a viral vaccine which induces HIV-specific T cell responses, and which is further capable of inducing CTL and CD4+ T helper cell responses, would be of great utility in the treatment of HIV-infected individuals.

Picornaviruses are attractive for use as viral vaccine vectors since they induce B and T cell immunity. In addition, the enteroviruses belonging to the Picornaviridae family, which include poliovirus and coxsackievirus, are known to induce mucosal immunity which is thought to be an important line of defense for pathogens (including HIV) that gain access via a mucosal port of entry. Thus, coxsackieviruses in particular should be considered.

Coxsackieviruses are subdivided into two serogroups, A and B, which comprise 24 and 6 serotypes, respectively (Rueckert, R. R., Fundamental Virology. 3rd ed. Philadelphia: Lippincott-Raven, 1996). Coxsackieviruses of the B group have been implicated in diseases such as pancreatitis, type I insulin-dependent diabetes mellitus, myocarditis and myositis. The existence of variants within a single serotype contributes to the variability in the pathogenesis of coxsackievirus infections. An avirulent coxsackievirus would be a suitable candidate for in vivo expression of HIV sequences capable of stimulating both CTL and CD4+ T helper cell responses.

Picornaviruses, which include coxsackievirus, are among the smallest RNA viruses, with a diameter of 30 mm (reviewed in (Metnick, J. L., Fields Virology. In: Fields B N, Knipe D M, Howley P M, et al. editors. Third ed. Philadelphia: Lippincott-Raven Publishers, 1996: 655-705). The coxsackievirus virion consists of a protein shell surrounding an RNA genome. The protein shell contains sixty copies of each of four capsid proteins, VP1, VP2, VP3 and VP4 that form an icosahedron. The enteroviral genome consists of a single-stranded RNA of positive polarity. Excluding the poly(A) tract, the genome-of coxsackievirus B4 consists of 7,395 nucleotides and is composed of a 5' untranslated (UTR) region of 743 nucleotides, a 3' UTR of 105 nucleotides and an open reading frame encoding a polyprotein of 2,183 amino acids which undergoes multiple cleavages (Jenkins et al., *J. Gen. Virol.* 68: 1835-1848 (1987)). The open reading frame is divided into three regions, P1, P2 and P3. The four capsid proteins, VP1 through VP4, are encoded within the P1 region while the non-structural proteins that are involved in viral replication are encoded within the P2 and P3 regions. Two B cell epitopes within the VP1 coat protein of CB4-V have recently been identified (Halim and Ramsingh, *Virol.* 269: 86-94 (1999)). A linear B cell epitope spans residues 68 to 82 that corresponds to parts of beta strand B and the BC-loop. A conformational epitope, analogous to antigenic site 1B of poliovirus, is predicted to contain sequences from both the DE- and BC-loops of VP1.

Efforts to exploit the picornaviruses as expression vectors have focused mainly on poliovirus. Several strategies have been used to express a variety of sequences within poliovirus vectors. Small antigenic epitopes have been expressed within the BC-loop of the VP1 capsid protein (Dedieu et al., *J. Virot.* 66: 3161-3167 (1992); Evans et al., *Nature* 339: 385-388 (1989); Jenkins et al., *J. Virot.* 64: 1201-1206 (1990); Murdin et al., *Infect. Immun.* 61: 4406-4414 (1993)). The resulting chimeras were either genetically stable, genetically unstable or non-viable. The stability of the recombinants seemed to depend on the retention of some flanking viral loop sequences and the size of the inserted sequence.

Two approaches have been used to generate live poliovirus vectors. One approach expresses foreign sequences in dicistronic vectors containing an additional internal ribosome entry site (IRES) (Lu et al., *J. Virol.* 69: 4797-4806 (1995)). While the dicistronic vector system resulted in replication-competent viruses, they were genetically unstable after just a few passages in tissue culture. Another strategy positions foreign sequence, flanked by artificial protease cleavage sites, at different sites within the polyprotein (Andino et al., *J. Virot.* 72: 20-31 (1994)). A larger than normal precursor polyprotein is synthesized and subsequently cleaved into its normal products and the foreign protein. Lately, some controversy has arisen regarding the utility of this strategy. Recombinants constructed by fusing the open reading frame (ORF) of the green fluorescent protein gene or the gag gene to the N-terminus of the poliovirus polyprotein were severely impaired in viral replication and genetically unstable (13). It is known that the site of insertion of the foreign sequence influenced viral replication (Tang et al., *J. Virot.* 71: 7841-7850 (1997)). A small amino-terminus insertion delayed virus maturation and yielded a thermosensitive particle. However, insertion at the junction between the P1 and P2 regions yielded a chimeric poliovirus that replicated like the wild type virus. While genetic instability remained a problem, the situation could be partially alleviated by altering the sequences flanking the insertion point. However, since poliovirus has been targeted for global eradication, the feasibility of using live poliovirus as a vector becomes uncertain.

Recent studies have led to the identification of an attenuated-live coxsackievirus variant, CB4-P (Ramsingh et al., *Virus Res.* 14: 347-58 (1989); Caggana et al., *J. Virol.* 67: 4797-803 (1993); Ramsingh et al., *J. Virol.* 71(11): 8690-7 (1997)). The major determinant of virulence was mapped to the 5' end of the viral genome through the use of recombinant chimeric viruses derived from cDNA clones of the CB4-P variant and a virulent virus. The 5' end of the genome encompasses both the 5' untranslated region (UTR) and the P1 region, which encodes the four capsid proteins (Ramsingh et al., *Virus Res.* 23: 281-92 (1992)). Comparison of sequence data in the 5' region between the CB4-P variant and a virulent pancreatropic variant of coxsackievirus, CB4-V, revealed five mutations in the CB4-P variant that resulted in amino acid substitutions in VP1, VP2, and VP4. In particular, one residue, Thr-129 of VP1, is a major determinant of virulence in the 5'UTR for coxsackievirus B4 (Caggana et al., *J. Virol.* 67: 4797-803 (1993)). An arginine residue at position 16 of VP4 also influences virulence but to a lesser extent than thr-129 of VP1 (Ramsingh and Collins, *J. Virol.* 69: 7278-7281 (1995)). The potential of this variant for use as a viral vector for delivery of heterologous polypeptides to a host has yet to be explored.

At least one attenuated strain of coxsackievirus has been used experimentally as a recombinant viral vaccine. Group B coxsackieviruses (CVB) cause human myocarditis, in which human adenovirus type 2 (Ad2) has been implicated as an agent. It has recently been demonstrated that an attenuated group B coxsackieviruses type 3 (CVB3) vector can stably express an antigenic polypeptide of Ad2 from within the vector open reading frame to ultimately elicit a protective immune response against both viruses in mice (Hofling et al., *J. Virol.* 74: 4570-8 (2000)).

SUMMARY OF THE INVENTION

One aspect of the present invention relates to a recombinant attenuated coxsackievirus B4 virion which is engineered to contain a heterologous nucleic acid within the open reading frame of its genome, wherein the heterologous nucleic acid encodes a heterologous polypeptide which is expressed by the virion. Specific examples of attenuated coxsackievirus B4 virions suitable for use in the present invention are CB4-P and JVB. In one embodiment the heterologous nucleic acid is inserted into the P1 region of the genome such that the heterologous polypeptide is expressed as a fusion of a viral capsid protein.

Another aspect of the present invention relates to a nucleic acid comprising the complete genome of the recombinant attenuated coxsackievirus B4 virion which is engineered to contain a heterologous nucleic acid within the open reading frame of its genome, wherein the heterologous nucleic acid encodes a heterologous polypeptide which is expressed by the virion. The nucleic acid is preferably an infectious cDNA or RNA.

Another aspect of the present invention relates to a method for inducing an immune response in an individual to the heterologous polypeptide which is expressed by the recombinant attenuated coxsackievirus B4 virion. The method comprises administering the recombinant attenuated coxsackievirus B4 virion to the individual under conditions appropriate for infection. In a preferred embodiment, the heterologous polypeptide is an antigen derived from a viral pathogen, preferably HIV.

Another aspect of the present invention relates to a method for delivering the heterologous polypeptide expressed by the recombinant attenuated coxsackievirus B4 virion to an individual. The method comprises administering the recombinant attenuated coxsackievirus B4 virion to the individual under conditions appropriate for infection.

The present invention is directed to a recombinant attenuated coxsackievirus B4 virion, such as JVB/CB4P, which is engineered to contain a heterologous nucleic acid within the open reading frame of its genome, wherein the heterologous nucleic acid encodes a heterologous polypeptide which is expressed by the virion. The heterologous nucleic acid is preferably in the P1 region of the genome. The heterologous nucleic acid is preferably in frame with the coding region such that the heterologous polypeptide is expressed as a fusion of a viral capsid protein, preferably expressed within an immunogenic region of the viral capsid protein, preferably VP1. The heterologous nucleic acid is preferably expressed as an internal fusion of VP1.

In the above recombinant virion, the immunogenic region of VP1 preferably contains B-cell epitopes, T-cell epitopes, or both. The heterologous polypeptide is preferably expressed within the viral capsid protein VP1 at a position which corresponds to the DE loop, preferably directly downstream of codon 129 of VP1 coding sequences. Preferably, the heterologous nucleic acid replaces nucleic acid sequences corresponding to VP1 codons 130-137.

In another embodiment of the recombinant virion, the heterologous nucleic acid is inserted in frame and directly upstream of sequences which encode VP4, preferably as an amino-terminal fusion of the viral polyprotein which may be directly after the first codon of the viral polyprotein. The insert may be from about 60 to about 360 nucleotides in length. In one embodiment, the amino-terminal fusion is susceptible to cleavage from the viral polyprotein by a viral protease.

The invention is also directed to a nucleic acid comprising the complete genome of a recombinant attenuated coxsackievirus B4 virion, such as JVB/CB4-P, which is engineered to contain a heterologous nucleic acid within the open reading frame of its genome, wherein the heterologous nucleic acid encodes a heterologous polypeptide which is expressed by the virion. This nucleic acid may be an infectious cDNA or infectious RNA of the viral genome. The heterologous nucleic acid is preferably inserted into the P1 region of the genome, more preferably into the coding region of VP1, such as into sequences which encode the DE loop of VP1. The heterologous nucleic acid insert may be directly downstream of codon 129 of VP1 coding sequences and replace codons 130-137 of VP1 coding sequences.

In another embodiment of the nucleic acid, the heterologous nucleic acid is inserted in frame and directly upstream of sequences which encode VP4, preferably directly after the first codon encoding VP4. The inserted heterologous nucleic acid may be from about 25 nucleotides to about 39 nucleotides in length. The insert preferably results in an antigenic polypeptide such as viral polypeptide or a fragment thereof when expressed in the context of the coxsackievirus B4 genome. The insert may further encode a T cell epitope, a B cell epitope, or both a T cell and a B cell epitope. The insert may encode a bacterial pathogen polypeptide or a fragment thereof. In a preferred embodiment, the insert encodes an HIV polypeptide or a fragment thereof, for example, HIV p24 or a fragment thereof.

The present invention is also directed to a method for inducing an immune response to a polypeptide in an individual, comprising: (a) providing a recombinant attenuated coxsackievirus B4 virion which is engineered to contain a heterologous nucleic acid within the open reading frame of its genome, wherein the heterologous nucleic acid encodes a heterologous polypeptide which is expressed by the virion; and (b) administering the recombinant attenuated coxsackievirus B4 virion to the individual under conditions appropriate for infection. In this method, the recombinant attenuated coxsackievirus B4 virion is formulated with a physiologically acceptable carrier. Preferably, the heterologous nucleic acid is expressed in the recombinant attenuated coxsackievirus B4 virion as an internal fusion of VP1 such that the heterologous nucleic acid is expressed within an immunogenic region of VP1. The immune response induced may comprise the generation of a cytotoxic T-cell response, a T helper cell response, B cell response, or any combination thereof.

In the above method, the heterologous nucleic acid is preferably expressed as an amino-terminal fusion of the viral polyprotein, which fusion may be susceptible to cleavage from the viral polyprotein by a viral protease. In the above method, the heterologous nucleic acid may further encode a T-cell epitope. In the above method for inducing an immune response, the heterologous polypeptide may be a polypeptide or fragment thereof from a pathogen of the individual. The immune response which is generated in the individual preferably prevents or inhibits disease progression in the individual. The polypeptide is preferably a viral polypeptide, such as an HIV polypeptide, preferably HIV polypeptide p24 or a fragment thereof. In the above method, the individual is an animal or a human who may be immunocompromised.

The present invention provides a method for inducing an immune response in an individual which is protective against coxsackievirus B4, comprising: (a) providing a recombinant coxsackie virion of the invention; and (b) administering the virion to the individual under conditions appropriate for infection.

Also included is a method for delivering a polypeptide to an individual, comprising:
  (a) providing a recombinant attenuated coxsackievirus B4 virion which is engineered to contain a heterologous nucleic acid within the open reading frame of its genome, wherein the heterologous nucleic acid encodes a heterologous polypeptide which is expressed by the virion, wherein the heterologous nucleic acid is expressed as an amino-terminal fusion of viral polyprotein wherein the amino-terminal fusion is susceptible to cleavage from the viral polyprotein by a viral protease; and
  (b) administering the recombinant attenuated coxsackievirus B4 virion of step (a) to the individual under conditions appropriate for infection.

BRIEF DESCRIPTION OF THE DRAWINGS

FIG. 1 shows the predicted DE-loop of VP1 of CB4-P contains a T helper cell epitope. Splenic CD4 T cells from CB4-P-infected BALB/c mice (closed symbols) or uninfected mice (open symbols) were tested in a proliferation assay. A total of eight mice were infected with CB4-P. Results of four infected mice are shown. (A) T cell proliferation in response to a viral peptide, 122P, spanning residues 122 to 136 of VP1 of CB4-P. (B) T cell proliferation in response to CB4-P and an unrelated peptide. An unrelated sequence, a peptide of the ryanodine receptor (RyR) SEQ ID NO: 1 (RAENEKDATTEKNKKR) (accession number, CAA49225) was used at two different concentrations (1 μg/well, 5 μg/well). Samples were analyzed in duplicate and the mean values are shown. (C) Antigenic structure of the predicted BC- and DE-loops of VP1 of CB4-P. Previous work identified a linear B cell epitope (site 1) spanning residues 75-82 and a conformational B cell epitope that may be analogous to site 1B of poliovirus. The T helper cell epitope, identified in panel (A) with peptide 122P, is outlined in bold.

Amino acid substitutions in the VP1 vector and in CB4-P/ova10 are in bold. The ovalbumin sequence in CB4-P/ova10 is in lower case.

Figure 3:
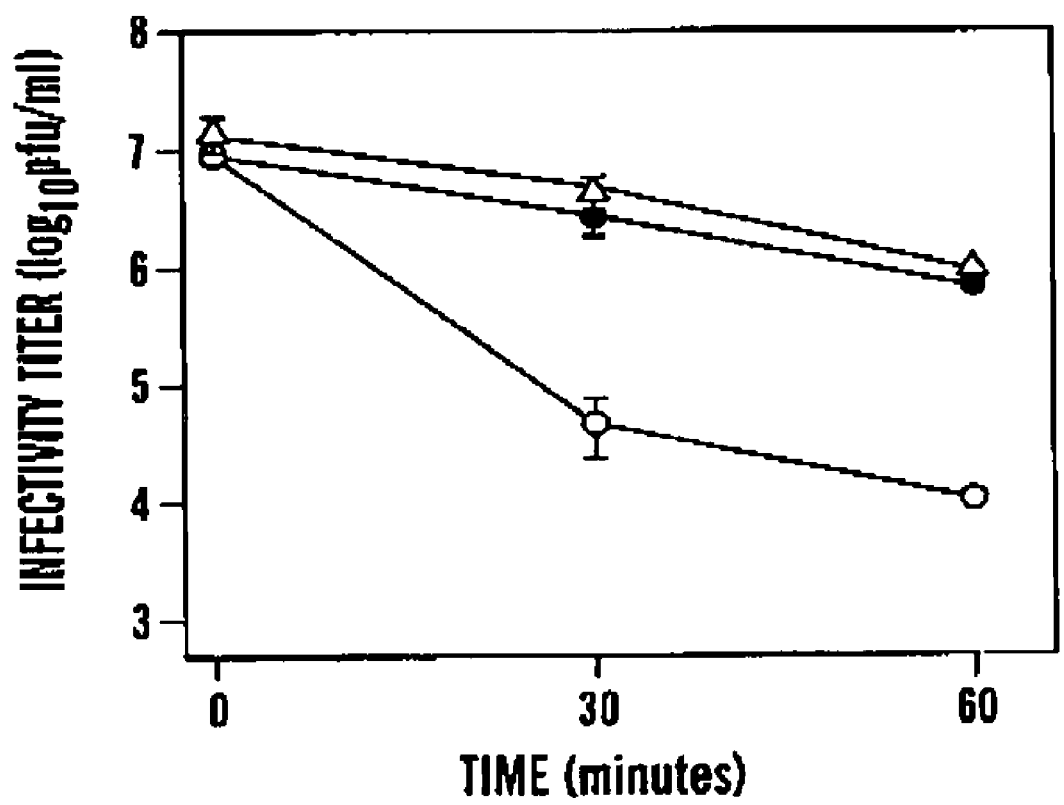

FIG. 3 shows the thermostability of a recombinant, chimeric coxsackievirus. Aliquots of CB4-P(•), CB4-V (○), and CB4-P/ova10 (Δ) were heat-inactivated at 44° for 30 and 60 minutes. Residual infectivity was assessed by plaque assay. Experiments were done twice and the mean values and standard deviations are shown.

FIG. 4 shows the replication of a chimeric coxsackievirus in vitro and in vivo. (A) Viral replication under single-step conditions. Each experiment was done a total of three times. The mean values and standard deviations are shown. (B) Viral replication in pancreatic tissues of mice. Pancreatic tissues were harvested from groups of three B10.S(12R) mice and tested individually for infectious virus. The mean and standard deviations are shown. •, CB4-P; Δ, CB4-P/ova10.

FIG. 5 (SEQ ID NOS: 21, 3 & 2, respectively in order of appearance) shows CD4 T cells from CB4-P/ova10-infected mice proliferated in response to ovalbumin peptides. Splenic CD4 T cells from BALB/c mice infected with CB4-P/ova10 (closed symbols) or CB4-P (open symbols) were tested in a proliferation assay for their ability to respond to ovalbumin peptides. Groups of eight mice were infected with each virus. Results of groups of four mice are shown. (A) Ovalbumin peptides tested in the proliferation assay. The ova/virus14 peptide is contained within the CB4-P/ova10 recombinant and contains 10 amino acids of ovalbumin sequence flanked by two amino acids of viral sequence. The OVA 323-339 peptide and the CB4-P/ova 10 recombinant share 11 common amino acids, three conserved residues (dots), and three non-conserved residues. The core sequence of ovalbumin that is critical for binding to I-A$^d$ is boxed. The predicted DE-loop of VP1 of the recombinant is bolded. (B) T cell proliferation in response to the ova/virus14 peptide. (C) T cell proliferation in response to OVA 323-339. (D) T cell proliferation in response to CB4-P, CB4-P/ova10 and an unrelated peptide (RyR). Samples were analyzed in duplicate and the mean values are shown.

FIG. 6 shows an avirulent variant, CB4-P, can protect against infection with a virulent virus, CB4-V. Pancreatic tissues, harvested two weeks after the second injection, were processed for histology and stained with hematoxylin and eosin. (A) uninfected; (B) PBS then CB4-P, 2 weeks later; (C) PBS then CB4-V, 2 weeks later; (D) CB4-P then CB4-V, 2 weeks later. Abbreviations: A, acinus; IL, islet of Langerhans; In, inflammatory infiltrate. Magnification, 160×.

Figure 7:
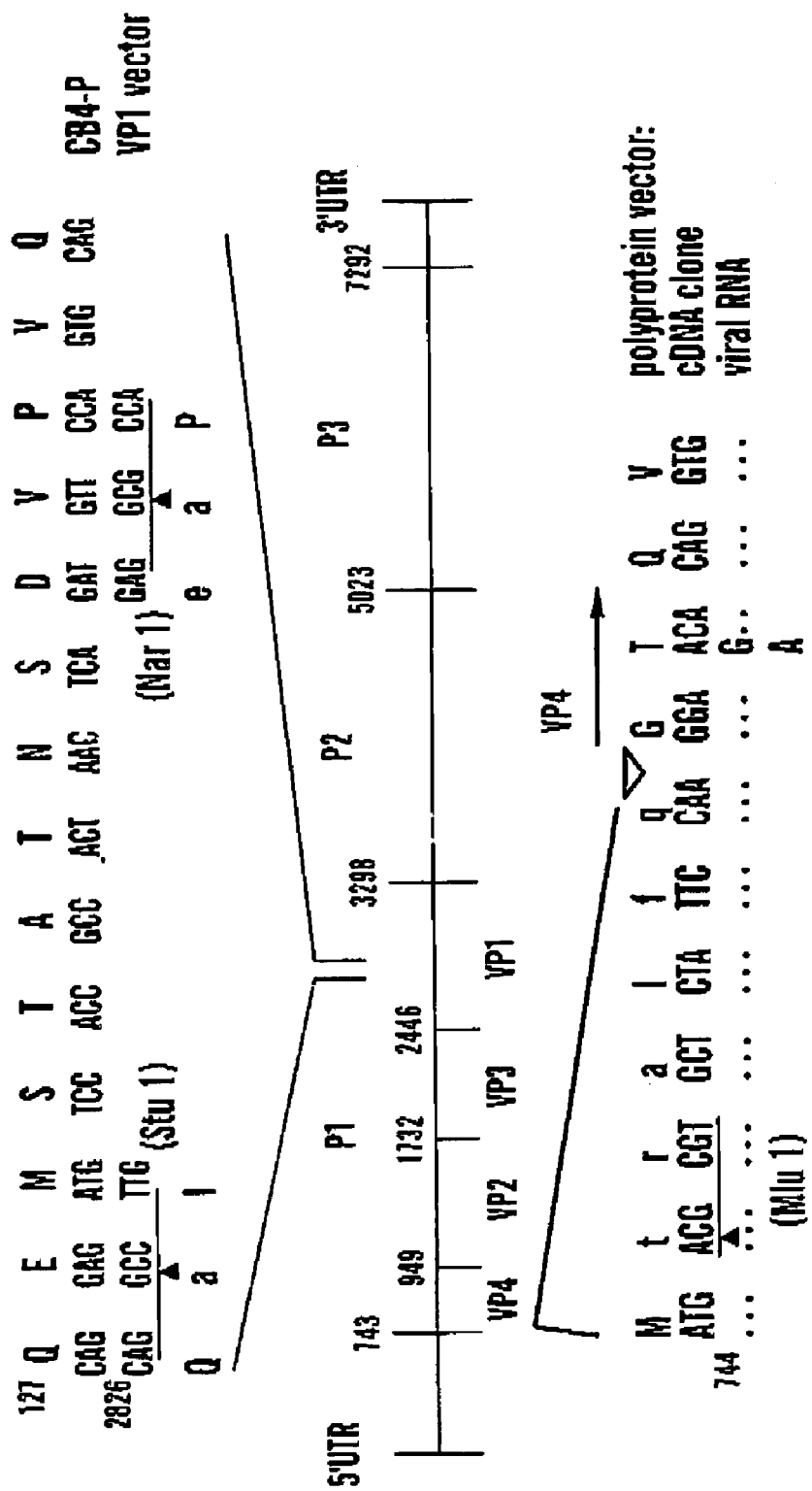

FIG. 7 (SEQ ID NOS: 15-18 & 22-25) shows construction of two coxsackievirus vectors for expressing foreign sequences within the VP1 capsid protein and at the amino-terminus of the viral polyprotein. A schematic representation of the structural organization of the coxsackievirus B4 (JVB strain) genome is shown. The predicted DE-loops of VP1 of CB4-P and the VP1 cassette vector, spanning amino acid residues 128 to 140, are shown. The VP1 cassette vector was constructed by introducing two unique restriction enzyme sites (StuI, NarI sites) (underlined) into a full-length infectious cDNA clone of CB4-P. Amino acid substitutions are in lower case. The polyprotein cassette vector was constructed by inserting an MluI cloning site (underlined) and a sequence encoding a recognition site (in bold) for the 3C protease immediately after the initiator codon of the VP4 sequence. The additional six amino acids in the polyprotein cassette vector are in lower case.

FIG. 8 (SEQ ID NOS: 26-28, respectively in order of appearance) shows recombinant, chimeric coxsackieviruses containing nine and ten amino acids of HIV p24 sequence within the DE-loop of the VP1 capsid are genetically stable. After six passages in LLC-MK2(D) cells, the genetic stability of the recombinants was assessed by sequence analysis. Total RNA was extracted from infected cells, reverse transcribed, amplified by PCR and sequenced. At least 200 bases on either side of the insert was sequenced. Mutations were not observed in the flanking sequences. Dots indicate identity and dashes indicate gaps. HIV sequences are in bold.

FIG. 9 (SEQ ID NOS: 29-32) shows recombinant, chimeric coxsackieviruses containing 35 and 62 amino acids of HIV p24 sequence, at the amino-terminus of the viral polyprotein are genetically stable. After six passages in LLC-MK2(D) cells, the genetic stability of the recombinants was assessed by sequence analysis. Total RNA was extracted from infected cells, reverse transcribed, amplified by PCR, and sequenced. At least 200 bases on either side of the insert was sequenced. A point mutation in the VP4 sequence was observed in both recombinants. Dots indicate identity and dashes indicate gaps. The MluI cloning site is underlined. The inserted protease site is boxed.

Figure 10:
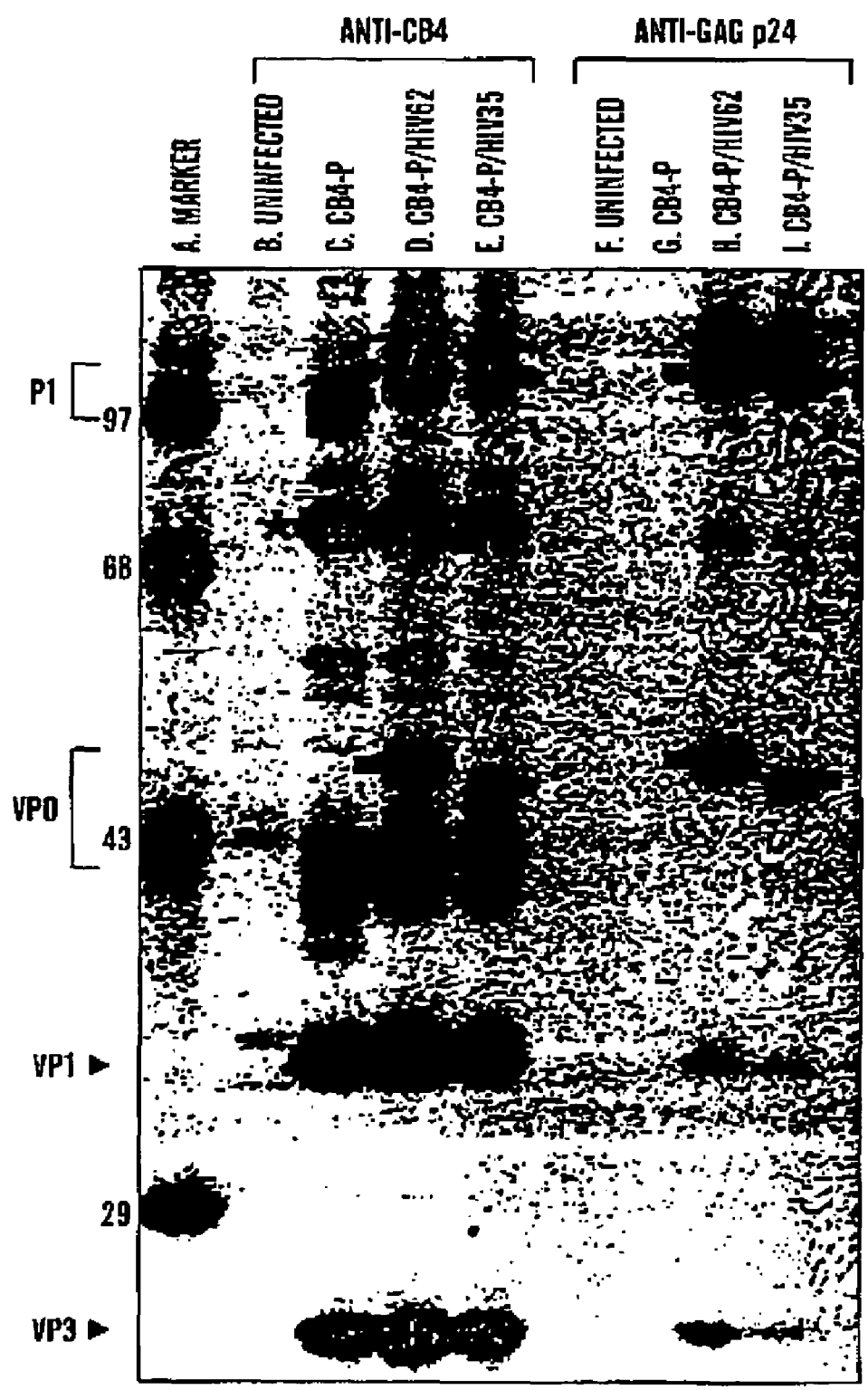

FIG. 10 shows expression of HIV p24 sequences in cells infected with CB4-P/HIV recombinants. Cells were infected with CB4-P, CB4-P/HIV35, and CB4-P/HIV62 and radiolabeled. Lysates were immunoprecipitated with anti-CB4 (lanes B-E) and anti-gag p24 (lanes F-1) antibodies. Larger versions of the P1 precursor (circles) and VP0 (squares) were detected, with both antibodies, in cells infected with the recombinants. An incompletely processed P1 precursor is identified with an asterisk.

Figure 11A:
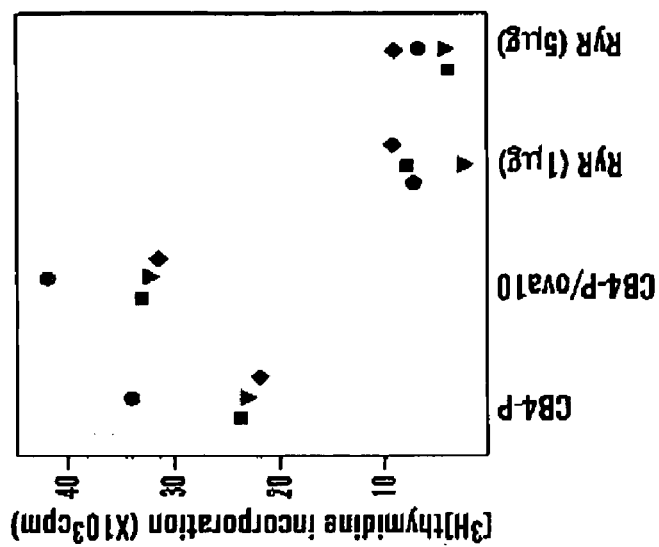
Figure 11B:
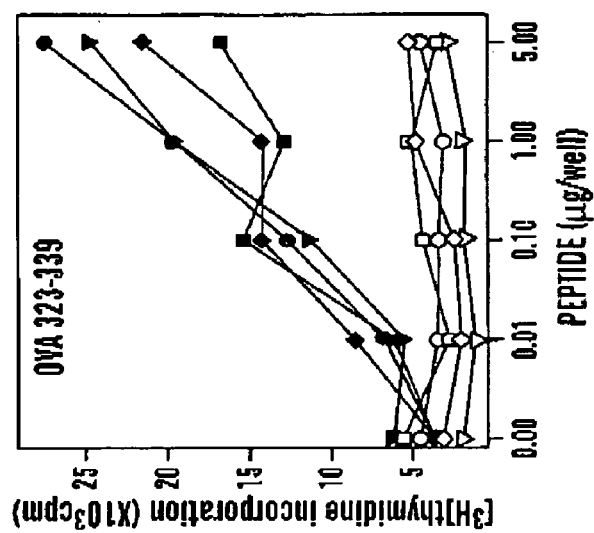
Figure 11C:
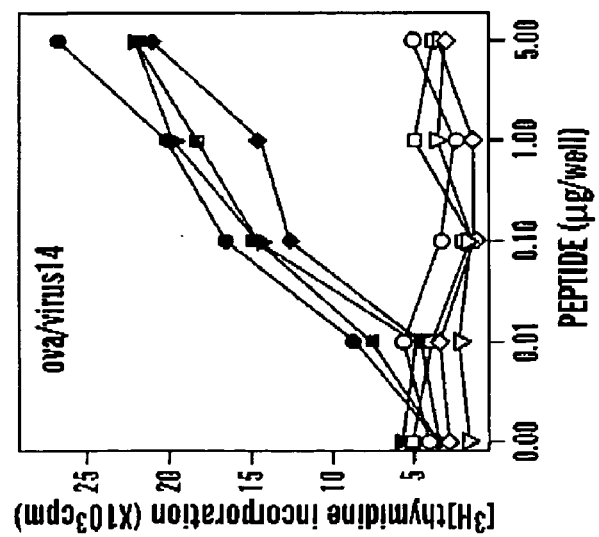

FIG. 11 shows CD4+ T cells from mice infected with CB4-P and later with the CB4-P/ova10 recombinant proliferated in response to ovalbumin peptides. Splenic CD4+T cells from doubly-infected mice (closed symbols) or mice infected with only CB4-P (open symbols) were tested in a proliferation assay for their ability to respond to ovalbumin peptides. Groups of eight mice were doubly- or singly-infected. Results of groups of four mice are shown. (A) T cell proliferation in response to a chimeric ova/virus peptide (SEQ ID NO: 2) (EMISQAVHAAHAEA) (viral amino acids are in italics). (B) T cell proliferation in response to OVA 323-339 (SEQ ID NO: 3) (ISQAVHAAHAEINEAGR). (C) T cell proliferation in response to CB4-P, CB4-P/ova10 and an unrelated peptide (RyR). Samples were analyzed in duplicate and the mean values are shown.

Figure 12:
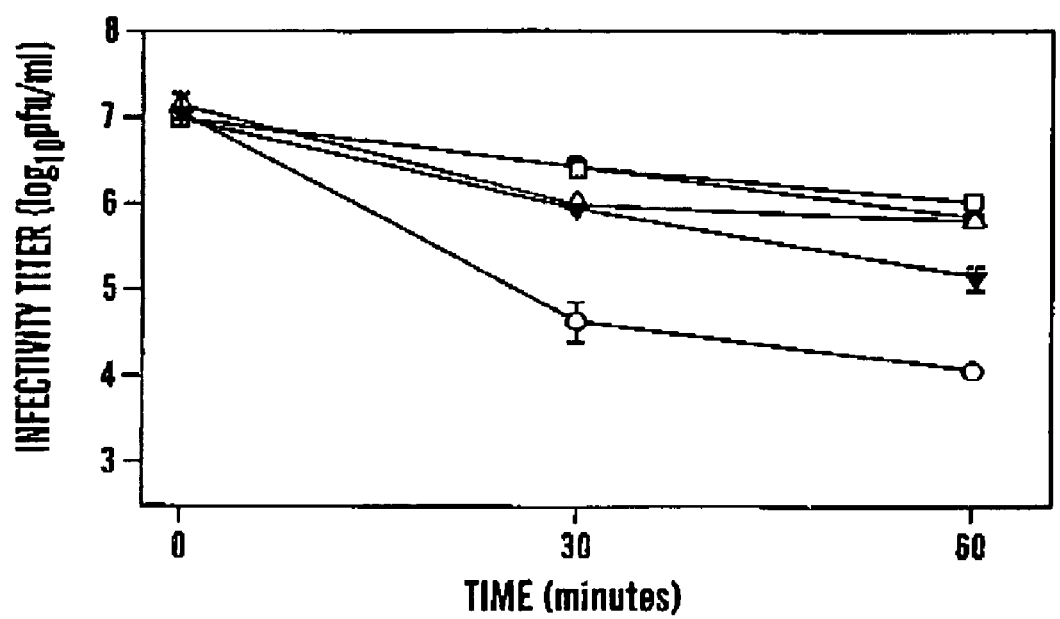

FIG. 12 shows CoxsackieJHIV chimeric viruses retain the thermostable phenotype of the parental CB4-P variant. Aliquots of virus were heat-inactivated at 44° C. for 30 and 60 minutes. Residual infectivity was assessed by plaque assay. Experiments were done twice and the mean values and standard deviations are shown. CB4-P (●; CB4-V (○); CB4-P/HIV9$_{104}$ (▼); CB4-P/HIV35 (Δ); and CB4-P/HIV62 (□).

Figure 13A:
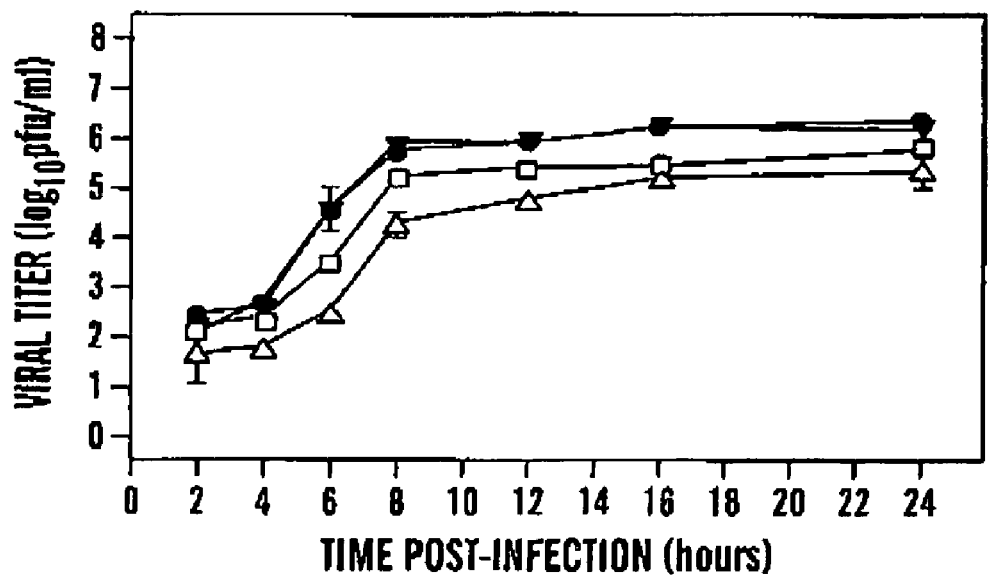

FIG. 13 shows replication of the coxsackie/HIV recombinants in cell culture and in mice. (A) Viral replication under single-step conditions. LLC-MK2(D) cells were infected at a multiplicity of infection of 2-5 pfu per cell. Virus was harvested after repeated freezing and thawing of infected cells. Each experiment was done a total of three times. The mean values and standard deviations are shown. (B) Viral replication in pancreatic tissues of mice. Pancreatic tissues were harvested from groups of three B10.S(12R) mice and tested individually for infectious virus. The mean and standard deviations are shown. CB4-P (●); CB4-P/HIV9$_{104}$ (▼); CB4-P/HIV35 (Δ); and CB4P/HIV62 (□).

FIG. 14 shows histological assessment of pancreatic tissue injury after infection with CB4-P/HIV35 and CB4-P/HIV62. Pancreatic tissues were harvested at different times post-infection (p.i.) and processed for routine histology and stained with hematoxylin and eosin. (A-C) 4 days p.i; (D-F) 10 days p.i. A,D. CB4-P; B,E. CB4-P/HIV35; C,F. CB4-P/HIV62. Less damage was observed in tissues from mice infected with the recombinants. Abbreviations: A, acinus; IL, islet of Langerhans; In, inflammatory infiltrate. Magnification, 127×.

DETAILED DESCRIPTION OF THE INVENTION

The term "live" as used herein to describe a virus, refers to a virus which is capable of self-propagation when placed in the appropriate cellular environment. The term "subunit vaccine" is used herein, as in the art, to refer to a viral vaccine that does not contain virus, but rather contains one or more viral proteins or fragments of viral proteins. As used herein, the term "multivalent" means that the vaccine contains at least two epitopes having different amino acid sequences.

Aspects of the present invention are based on the discovery that a live, attenuated group B, type 4, coxsackievirus (referred to herein as CB4) virion can be used to express a heterologous polypeptide (e.g., in vitro or in a host organism). Such a virus, engineered to express the heterologous polypeptide is referred to herein as a coxsackievirus vector, a CB4 vector, or a viral vector.

One aspect of the present invention relates to a CB4 vector. The CB4 vector is a recombinant attenuated CB4 virion which is engineered to contain a heterologous nucleic acid within the its genome such that the heterologous nucleic acid encodes a heterologous polypeptide which is expressed by the virion. (The term "heterologous polypeptide" refers to a polypeptide which is not otherwise naturally expressed by the virus. The term "heterologous nucleic acid" refers to any nucleic acid which is not otherwise naturally present in the genome of the virus at the position in which it is inserted.) The heterologous nucleic acid is inserted into the genome of the CB4 virion by recombinant DNA technology, preferably into the open reading frame of the viral genome, preferably such that it is inframe with the viral open reading frame. In one embodiment, the heterologous nucleic acid is inserted into the P1 region of the genome, which encodes the viral capsid proteins.

The coxsackievirus variant CB4-P has been used as a prototype to demonstrate that an attenuated coxsackievirus B4 virion can be successfully engineered to stably express a heterologous protein in a host. The terms "stably expressed" and "stable expression", as used herein, refer to expression of the heterologous polypeptide from the viral vector for a duration sufficient to be of therapeutic use. This may be as short as 3-5 replication cycles of the virus, or alternatively may be a greater number of replication cycles. It was not heretofore known whether stable expression of foreign sequences could be obtained from an attenuated B4 coxsackievirus. Furthermore, because there is a high incidence of neutralizing antibody in the general population to group B coxsackieviruses (Pallansch, M. A., *Curr. Topics Microbiol. Immunol.:* 22313-30 (1997)), it was not known heretofore whether pre-existing immunity to the virus would affect subsequent administration of the viral vector, or expression of the heterologous polypeptide contained therein. The findings made with the CB4-P virus apply to any attenuated B4 coxsackievirus. Thus all embodiments of the present invention described herein, are intended to equivalently apply to viral vectors made from any attenuated B4 coxsackievirus. Determination that a given strain or variant of B4 coxsackievirus is attenuated (non-pathogenic and avirulent) is made, for example, by characterization of that virus in mice, as discussed in Example 2 below. One example of such an attenuated B4 coxsackievirus is J.V.B. (Benschoten), ATCC reference number 184 (referred to herein as JVB). The prototype virus CB4-P is originally derived from JVB and is highly similar to JVB in nucleotide and amino acid sequence. Because of this strong conservation, the JVB virus is expected to perform as an equivalent to CB4-P in the generation and use of the viral vector described herein.

The term "wild type" as used herein, refers to the B4 coxsackievirus, prior to any recombinant manipulations made to produce the viral vector. Through sequence alignment, one of skill in the art can identify nucleotide and amino acid sequences of other CB4 viruses (e.g., JVB) which correspond to the nucleotides or amino acids of CB4-P. Such a determination falls within the definition of routine experimentation.

The point within the viral genome at which the heterologous nucleic acid is inserted will directly effect the protein product which is expressed. Insertion of the heterologous nucleic acid in frame with viral coding sequences leads to the exogenous polypeptide being expressed as a fusion with viral proteins. Such a fusion can be an N-terminal fusion, a C-terminal fusion, or an internal fusion (e.g., where the exogenous polypeptide is flanked on both sides by viral polypeptide). In one embodiment the exogenous polypeptide is expressed as a fusion with a viral capsid protein. Such an fused polypeptide may be any size useful in the generation of an immune response to that polypeptide. Preferably it is at least 5 amino acids in length. Genetic stability of a heterologous nucleic acid inserted into the virus genome to produce a fused heterologous polypeptide is expected to be highest if it is at least 24 nucleotides in length and no greater than 39 nucleotides. However larger and smaller inserts may still retain sufficient genetic stability to be considered therapeutically useful.

Fusion of the exogenous polypeptide at an immunogenic portion of the viral capsid protein (e.g., adjacent a region which contains T cell epitopes and/or B cell epitopes) results in the exogenous polypeptide being immunogenic in the host, such that it elicits a T cell and/or B cell response. One of skill in the art will recognize that such an exogenous polypeptide itself may be non-antigenic in another context. A viral vector which contains such an insertion is expected to elicit both a cytotoxic T cell and a T helper cell response to the heterologous polypeptide. In one embodiment, the heterologous polypeptide is expressed as an internal fusion of VP1, preferably within the BC or DE loop. In a preferred embodiment, the viral vector is constructed such that the heterologous nucleic acid is located directly downstream of codon 129 of VP1 coding sequences. The term "directly downstream" or "directly upstream", as used herein, indicates that the heterologous nucleic acid coding sequences are the next adjacent codon. A viral vector can also be produced by replacing short stretches of viral nucleotide sequences with the nucleotide sequences of the heterologous nucleic acid. For example, nucleotide sequences which correspond wild type CB4-P coding sequences for VP1 amino acids 130-137 can be replaced with the heterologous nucleic acid.

As an alternative to expressing the heterologous polypeptide as a fusion with viral protein sequences, the heterologous nucleic acid can be expressed as an isolated polypeptide. A isolated polypeptide is produced for instance if the exogenous polypeptide is expressed as part of the virus polyprotein at such a position that it is susceptible to cleavage by a viral protease. Such a viral vector is produced for example, by insertion of the heterologous nucleic acid in frame directly upstream of VP4 coding sequences. Such an insertion results in the generation of a heterologous polypeptide which is expressed as an amino-terminal fusion of the viral polyprotein. This amino-terminal fusion is subject to cleavage by viral proteases, and thus is ultimately expressed by the virus as an isolated polypeptide. In a preferred embodiment, the heterologous nucleic acid contains an ATG as it's first codon, to facilitate translation. Alternatively, it is inserted directly downstream of the first ATG of VP4.

Sizes of between 105-357 nucleotides are expected to be most stably maintained at such a position within the viral genome. Heterologous nucleic acids which are smaller or larger, may be less stable within the viral genome, but are still likely to be retained for several replication cycles (at least 4 replication cycles), and therefore are still of therapeutic value.

If the heterologous polypeptide is itself immunogenic (e.g., contains B cell epitopes and/or T cell epitopes) it will elicit an immune response in the host when expressed as an isolated polypeptide by the viral vector. Such a polypeptide is generally at least 15 amino acids in length, and preferably at least 20 amino acids in length. A heterologous polypeptide which is immunogenic, and is expressed in this manner, is expected to elicit at least a cytotoxic T cell response in the host.

Delivery of a polypeptide to a host individual is not however limited to applications for stimulating an immune response. The polypeptide may alternatively have another function within the host (e.g., enzymatic activity), as discussed below.

Another aspect of the present invention relates to a nucleic acid comprising the complete genome of the CB4 vector described herein. The nucleic acid may be DNA (such as a plasmid DNA) or RNA. Preferably, the nucleic acid is either an infectious cDNA or an infectious RNA of the CB4 vector genome, wherein infection results in the production of a live virion.

Another aspect of the present invention relates to a method for inducing an immune response to a polypeptide in an individual by administering a CB4 vector which expresses the polypeptide to the individual. For most applications, the CB4 vector is administered to the individual under conditions appropriate for infection. In some circumstances however, it may be preferable to inactivate the CB4 vector prior to administration to the individual. The individual may be any host vertebrate, as discussed below. The CB4 vector may be formulated with a physiologically acceptable carrier. A CB4 vector which expresses a heterologous polypeptide which is derived from a pathogen (e.g., virus, bacteria, parasite) of the individual may serve as an effective a vaccine for that pathogen. Such a vaccine may be used to produce protective immunity from infection, or alternatively to control a preexisting infection.

Experiments detailed in the Exemplification section below indicate that the coxsackievirus variant, CB4-P, remains avirulent in mice lacking CD4+ T helper cells. This finding has significant ramification as to uses of the viral vector in immunocompromised individuals, indicating that it is a safe and effective means of delivering an antigenic epitope to an immunocompromised individual. Such an application is highly relevant to delivery of an antigenic epitope to individuals infected with HIV. One such application is the therapeutic delivery of HIV antigens to an individual in order to inhibit or prevent disease progression.

Thus, a CB4 vector can be used to elicit broad responses against HIV. The herein discussed strategy with respect to HIV can also be employed with respect to other pathogens, such as pathogens that attacks the immune system and/or T-cells such as retroviruses, lentiviruses, and immunodeficiency viruses, such as HIV, SIV, FIV and the like.

Another aspect of the invention relates to the use of an attenuated CB4 virus, such as CB4-P, to produce immunity to a virulent CB4 virus. Since the CB4-P virus has been shown to be non-virulent in immunocompromised individuals, it has significant value as a live vaccine for virulent strains of B4 coxsackieviruses in such an individual.

Experiments detailed in the Exemplification section below indicate that a live, attenuated coxsackievirus B4-P variant can be used as an expression vector, from which an exogenous or heterologous or foreign epitope is expressed, advantageously from within the immunogenic CB4-P coat protein region of the genome, and wherein the vector is administered as an immunogenic vaccine composition in an amount and duration sufficient to induce in a subject a T cell response and/or an otherwise desired immunogenic response.

Aspects of the present invention also relate to CB4 vectors, expression products thereof and therapeutic, immunological, immunogenic or vaccine compositions thereof comprising the attenuated coxsackievirus B4 and/or the expression products, for instance, epitopic region(s), and/or polypeptide(s) and/or fragment(s) expressed therefrom (e.g., an exogenous or heterologous or foreign epitope such as HIV p24), whether expressed in vitro or in vivo.

As to the inserted exogenous nucleotide sequence in a viral vector of the invention, it preferably encodes an expression product comprising: an epitope of interest, a biological response modulator, a growth factor, a recognition sequence, a therapeutic gene or a fusion protein. With respect to these terms, reference is made to the following discussion, and generally to Kendrew, THE ENCYCLOPEDIA OF MOLECULAR BIOLOGY (Blackwell Science Ltd., 1995) and Sambrook, Fritsch and Maniatis, Molecular Cloning, A Laboratory Manual, 2nd Ed., Cold Spring Harbor Laboratory Press, 1982.

An epitope of interest is an immunologically relevant region of an antigen or immunogen or immunologically active fragment thereof (e.g., from a pathogen or toxin of veterinary or human interest). The term polypeptide fragment or protein fragment, as used herein, is defined as 5 or more contiguous residues of a larger protein (e.g., a naturally occurring protein).

An epitope of interest can be an antigen of a pathogen or toxin, or a portion of an antigen of a pathogen of toxin, or prepared from an antigen of a pathogen or toxin, or from another antigen or toxin which elicits a response with respect to the pathogen, or from another antigen or toxin which elicits a response with respect to the pathogen, such as, for instance: a Morbillivirus antigen (e.g., a canine distemper virus or measles or rinderpest antigen such as HA or F; a rabies glycoprotein, such as rabies glycoprotein G; an avian influenza antigen, such as turkey influenza HA, Chicken/Pennsylvania/l/83 influenza antigen such as a nucleoprotein (NP); a bovine leukemia virus antigen, such as gp5l,30 envelope; a Newcastle Disease Virus (NDV) antigen, such as HN or F; a feline leukemia virus antigen (FeLV), such as FeLV envelope protein; RAV-I env; matrix and/or preplomer of infectious bronchitis virus; a Herpesvirus glycoprotein, such as a glycoprotein from feline herpesvirus, equine herpesvirus, bovine herpesvirus, pseudorabies virus, canine herpesvirus, HSV, Marek's Disease Virus, or cytomegalovirus; a flavivirus antigen, such as a Japanese encephalitis virus (JEV) antigen, a Yellow Fever antigen, or a Dengue virus antigen; a malaria (Plasmodium) antigen, an immunodeficiency virus antigen, such as a feline immunodeficiency virus (FIV) antigen or a simian immunodeficiency virus (SIV) antigen or a human immunodeficiency virus antigen (HIV); a parvovirus antigen, such as canine parvovirus; an equine influenza antigen; an poxvirus antigen, such as an ectromelia antigen, a canarypox virus antigen or a fowlpoxvirus antigen; or an infectious bursal disease virus antigen, such as VP2, VP3, VP4; a Hepatitis virus antigen, such as HBsAg; a Hantaan virus antigen; a C. tetani antigen; a mumps antigen; a pneumococcal antigen, such as PspA; a Borrelia antigen, such as OspA, OspB, OspC of Borrelia associated with Lyme disease such as *Borrelia burgdorferi, Borrelia afzelli* and *Borrelia garinii;* or a chicken pox (*varicella zoster*) antigen). Preferably, the epitope is derived from HIV or coxsackievirus. More preferably, the epitope is derived from HIV p24.

Of course, the foregoing lists are intended as exemplary, as the epitope of interest can be derived from any antigen of any veterinary or human pathogen; and, to obtain an epitope of interest, one can express an antigen of any veterinary or human pathogen (such that the invention encompasses the exogenous or foreign nucleotide sequence(s) of interest encoding at least one antigen).

Since the heterologous nucleic acid can be a growth factor or therapeutic gene, the inventive recombinants can be used in gene therapy. Gene therapy involves transferring genetic information; and, with respect to gene therapy and immunotherapy, reference is made to U.S. Pat. No. 5,252,479, which is incorporated herein by reference, together with the documents cited in it and on its face, and to WO 94/16716 and U.S. Pat. No. 5,833,975 each of which is also incorporated herein by reference, together with the documents cited therein. The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin, macrophage colony stimulating factor, granulocyte colony stimulating factor, erythropoietin, mast cell growth factor, tumor suppressor p53, retinoblastoma, interferon, melanoma associated antigen or B7.

The invention further relates to an immunogenic, immunological or vaccine composition containing the inventive vector and an acceptable carrier or diluent (e.g., veterinary acceptable or pharmaceutically acceptable). An immunological composition containing the vector (or an expression product thereof) elicits an immunological response—local or systemic. The response can, but need not be protective. An immunogenic composition containing the inventive recombinants (or an expression product thereof) likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method of inducing an immunological response in a host vertebrate comprising administering to the host an immunogenic, immunological or vaccine composition comprising the inventive recombinant virus or vector and an acceptable carrier or diluent. For purposes of this specification, "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans. Thus, a "subject" is a "host vertebrate, preferably a mammal, and more preferably a human. Mammals include but are not limited to humans, farm animals (food producing animals such as pigs, goats, sheep, lambs, cows, and work producing animals such as horses, donkeys, asses, camels, llamas, and the like that may, in some cultures, also be considered useful for food), sport animals (e.g., horses, dogs and the like), and pets (e.g., companion animals such as cats, dogs and the like).

The heterologous nucleic acid can encode any of the aforementioned epitopes of interest, as listed above. In this regard, with respect to Borrelia DNA, reference is made to U.S. Pat. No. 5,523,089, WO93/08306, PCT/US92/08697, Molecular Microbiology (1989), 3(4): 479-486, and PCT publications WO 93/04175, and WO 96/06165, incorporated herein by reference. With respect to pneumococcal epitopes of interest, reference is made to Briles et al. WO 92/14488, incorporated herein by reference. With respect to tumor viruses reference is made to Molecular Biology of Tumor Viruses, RNA TUMOR VIRUSES (Second Edition, Edited by Weiss et al., Cold Spring Harbor Laboratory 1982) (e.g., page 44 et seq.—Taxonomy of Retroviruses), incorporated herein by reference. Further, with respect to nucleic acid encoding epitopes of interest, attention is directed to documents cited herein, see, for instance documents cited supra and documents cited infra, for instance: U.S. Pat. Nos. 5,174,993 and 5,505,941 (e.g., recombinant avipox virus, vaccinia virus; rabies glycoprotein (G), gene, turkey influenza hemagglutinin gene, gp5l, 30 envelope gene of bovine leukemia virus, Newcastle Disease Virus (NDV) antigen, FeIV envelope gene, RAV-I env gene, NP (nucleoprotein gene of Chicken/Pennsylvania/l/83 influenza virus), matrix and preplomer gene of infectious bronchitis virus; HSV gD), U.S. Pat. No. 5,338,683 (e.g., recombinant vaccinia virus, avipox virus; DNA encoding Herpesvirus glycoproteins, inter alia), U.S. Pat. No. 5,494,807 (e.g., recombinant vaccinia, avipox; exogenous DNA encoding antigens from rabies, Hepatitis B, JEV, YF, Dengue, measles, pseudorabies, Epstein-Barr, HSV, HIV, SIV, EHV, BHV, HCMV, canine parvovirus, equine influenza, FeLV, FHV, Hantaan, C. tetani, avian influenza, mumps, NDV, inter alia), U.S. Pat. No. 5,503,834 (e.g., recombinant vaccinia, avipox, Morbillivirus, e.g., measles F, hemagglutinin, inter alia), U.S. Pat. No. 4,722,848 (e.g., recombinant vaccinia virus; HSV tk, HSV glycoproteins, e.g., gB, gD, influenza HA, Hepatitis B, e.g., HBsAg, inter alia), U.K. Patent GB 2 269 820 B and U.S. Pat. No. 5,514,375 (recombinant poxvirus; flavivirus structural proteins); WO 92/22641 and U.S. Pat. No. 5,863, 542 (e.g., recombinant poxvirus; immunodeficiency virus, HTLV, inter alia), WO 93/03145, and U.S. Pat. Nos. 5,658, 572 and 5,641,490 (e.g., recombinant poxvirus; IBDV, inter alia), WO 94/16716 and U.S. Pat. No. 5,833,975 (e.g., recombinant poxvirus; cytokine and/or tumor associated antigens, inter alia), U.S. Pat. No. 5,529,780 and allowed U.S. Pat. No. 5,688,920 (canine herpesvirus), WO 96/3941 and PCT/US94/06652 (Plasmodium antigens such as from each stage of the Plasmodium life cycle); see also U.S. Pat. Nos. 4,603,112, 4,769,330, 5,174,993, 5,505,941, 5,338, 683, 5,494,807, 4,722,848, 5,942,335, 5,364,773, 5,762,938, 5,770,212, 5,942,235, 5,756,103, 5,766,599, 6,004,777, 5,990,091, 6,033,904, 5,869,312, 5,382,425, WO 94/16716, WO 96/39491, and documents cited therein for epitopes of interest and antigens that are desirable to express and exogenous nucleic acid molecules useful in the practice of the invention. The inventive vector preferably encodes at least regions of a peptide of interest that generate an antibody or T cell response; and, advantageously, an epitope comprises a peptide fragment of about 10-17 amino acids in length.

As to antigens for use in vaccine or immunological compositions, reference is made to the documents and discussion set forth in the documents cited herein; see also Stedman's Medical Dictionary (24th edition, 1982) for a definition of vaccine and for a list of antigens used in vaccine formulations. Such antigens or epitopes of interest from those antigens can be used in the invention, as either an expression product of an inventive recombinant virus or vector, or in a multivalent composition containing an inventive recombinant virus or vector or an expression product therefrom.

As to epitopes of interest, one skilled in the art can determine an epitope or immunodominant region of a peptide or polypeptide and ergo the coding nucleic acid therefor from the knowledge of the amino acid and corresponding nucleic acid sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, Essential Immunology, 1988.

As to size: the skilled artisan can maximize the size of the protein encoded by the DNA sequence to be inserted into the viral vector (keeping in mind the packaging limitations of the vector). To minimize the nucleic acid inserted into the vector while maximizing the size of the protein expressed, the nucleic acid sequence inserted can exclude intron nucleotide sequences (regions of a gene which are transcribed but which are subsequently excised from the primary RNA transcript).

At a minimum, the heterologous nucleic acid can code for a peptide at least 8 or 9 amino acids long. This is the minimum length that a peptide needs to be in order to stimulate a CD8+T cell response (which recognizes virus infected cells or cancerous cells). This nucleic acid may be contain coding sequences derived from two different sources, (e.g., coding for a fragment of a protein of interest and also a T-cell epitope derived from another source) include coding sequences which encode a minimum peptide length of 13 to 25 amino acids is useful to stimulate a CD4+T cell response (which recognizes special antigen presenting cells that have engulfed the pathogen), see Kendrew, supra. However, as these are minimum lengths, these peptides are likely to generate an immunological response, such as an antibody or T cell response, but, for a protective response (as from a vaccine composition), a longer peptide may be preferred.

With respect to the sequence of the heterologous nucleic acid, it preferably encodes at least regions or a fragment of a peptide that generates an antibody response or a T cell response. One method to determine T and B cell epitopes involves epitope mapping. The protein of interest is synthesized in short overlapping peptides (PEPSCAN), or the protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. The method may be less-effective for determining B-cell epitopes" since B cell epitopes are often not linear amino acid sequence but rather result from the tertiary structure of the folded three dimensional protein. Janis Kuby, Immunology, (1992) pp. 79-80.

Another method for determining an epitope of interest is to choose the regions of the protein that are hydrophilic. Hydrophilic residues are often on the surface of the protein and are therefore often the regions of the protein that are accessible to the antibody. Janis Kuby, Immunology, (1992) p. 81. Yet another method for determining an epitope of interest is to perform an X-ray crystallographic analysis of the antigen (full length)-antibody complex. Janis Kuby, Immunology, (1992) p. 80. Still another method for choosing an epitope of interest which can generate a T cell response is to identify from the protein sequence potential HLA anchor binding motifs which are peptide sequences which are known to be likely to bind to the MHC molecule.

The peptide that is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatibility complex MHC" located on another cell's surface. There are two classes of MHC complexes—class I and class II, and each class is made up of many different alleles. Different patients have different types of MHC complex alleles; they are said to have a 'different HLA type.'

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD8 on their surface, bind specifically to the MHC class I/peptide complexes via the T cell receptor. This leads to cytolytic effector activities.

Class II MHC complexes are found only on antigen-presenting cells and are used to present peptides from circulating pathogens which have been endocytosed by the antigenpresenting cells. T cells which have a protein called CD4 bind to the MHC class II/peptide complexes via the T cell receptor. This leads to the synthesis of specific cytokines that stimulate an immune response.

Some guidelines in determining whether a protein is an epitope of interest which will stimulate a T cell response, include: Peptide length—the peptide should be at least 8 or 9 amino acids long to fit into the MHC class I complex and at least 13-25 amino acids long to fit into a class II MHC complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia et al., *Blood* 85: 2680-2684; Englehard, V. H., *Ann. Rev. Immunol.* 12: 181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules. Also, the skilled artisan can understand, without undue experimentation, an immunogenic B or T cell response.

Further, the skilled artisan can ascertain an epitope of interest by comparing the protein sequence with sequences listed in the protein data base. Even further, another method is simply to generate or express portions of a protein of interest, generate monoclonal antibodies to those portions of the protein of interest, and then ascertain whether those antibodies inhibit growth in vitro of the pathogen from which the from which the protein was derived. The skilled artisan can use the other guidelines set forth in this disclosure and in the art for generating or expressing portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophilic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

With respect to expression of a biological response modulator, reference is made to Wohlstadter, "Selection Methods," WO 93/19170, published Sep. 30, 1993, and the documents cited therein, incorporated herein by reference. For instance, a biological response modulator modulates biological activity; for instance, a biological response modulator is a modulatory component such as a high molecular weight protein associated with non-NMDA excitatory amino acid receptors and which allosterically regulates affinity of AMPA binding (See Kendrew, supra). The recombinant of the present invention can express such a high molecular weight protein.

More generally, nature has provided a number of precedents of biological response modulators. Modulation of activity may be carried out through mechanisms as complicated and intricate as allosteric induced quaternary change to simple presence/absence, e.g., expression/degradation, systems. Indeed, the repression/activation of expression of many biological molecules is itself mediated by molecules whose activities are capable of being modulated through a variety of mechanisms. Table 2 of Neidhardt et al Physiology of the Bacterial Cell (Sinauer Associates Inc., Publishers, 1990), at page 73, lists chemical modifications to bacterial proteins. As is noted in that table, some modifications are involved in proper assembly and other modifications are not, but in either case such modifications are capable of causing modulation of function. From that table, analogous chemical modulations for proteins of other cells can be determined, without undue experimentation. In some instances modulation of biological functions may be mediated simply through the proper/improper localization of a molecule. Molecules may function to provide a growth advantage or disadvantage only if they are targeted to a particular location. For example, a molecule may be typically not taken up or used by a cell, as a function of that molecule being first degraded by the cell by secretion of an enzyme for that degradation. Thus, production of the enzyme by a recombinant can regulate use or uptake of the molecule by a cell. Likewise, the recombinant can express a molecule that binds to the enzyme necessary for uptake or use of a molecule, thereby similarly regulating its uptake or use. Localization targeting of proteins carried out through cleavage of signal peptides another type of modulation or regulation. In this case, a specific endoprotease catalytic activity can be expressed by the recombinant. Other examples of mechanisms through which modulation of function may occur are RNA virus poly-proteins, allosteric effects, and general covalent and non-covalent steric hindrance.

HIV is a well studied example of an RNA virus that expresses non-functional polyprotein constructs. In HIV "the gag, pol, and env poly-proteins are processed to yield, respectively, the viral structural proteins p 17, p24, and p15—reverse transcriptase and integrase—and the two envelope proteins gp41and gp120" (Kohl et al., *PNAS U.S.A.* 85: 4686-90 (1988)). The proper cleavage of the poly-proteins is crucial for replication of the virus, and virions carrying inactive mutant HIV protease are non-infectious (Id.). This is another example of the fusion of proteins down-modulating their activity. Thus, it is possible to construct recombinant viruses that express molecules which interfere with endoproteases, or which provide endoproteases, for inhibiting or enhancing the natural expression of certain proteins (by interfering with or enhancing cleavage). The functional usefulness of enzymes may also be modulated by altering their capability of catalyzing a reaction. Illustrative examples of modulated molecules are zymogens, formation/disassociation of multi-subunit functional complexes, RNA virus poly-protein chains, allosteric interactions, general steric hindrance (covalent and non-covalent) and a variety of chemical modifications such as phosphorylation, methylation, acetylation, adenylation, and uridenylation (see Table I of Neidhardt, supra, at page 315 and Table 2 at page 73).

Zymogens are examples of naturally occurring protein fusions which cause modulation of enzymatic activity. Zymogens are one class of proteins which are converted into their active state through limited proteolysis. See Table 3 of Reich, Proteases and Biological Control, Vol. 2, (1975) at page 54). Nature has developed a mechanism of down-modulating the activity of certain enzymes, such as trypsin, by expressing these enzymes with additional "leader" peptide sequences at their amino termini. With the extra peptide sequence the enzyme is in the inactive zymogen state. Upon cleavage of this sequence the zymogen is converted to its enzymatically active state. The overall reaction rates of the zymogen are "about $10^5$-$10^6$ times lower than those of the corresponding enzyme" (See Table 3 of Reich, supra at page 54). It is therefore possible to down-modulate the function of certain enzymes simply by the addition of a peptide sequence to one of its termini. For example, with knowledge of this property, a recombinant can express peptide sequences containing additional amino acids at one or both termini. The formation or disassociation of multi-subunit enzymes is another way through which modulation may occur. Different mechanisms may be responsible for the modulation of activity upon formation or disassociation of multi-subunit enzymes. Therefore, sterically hindering the proper specific subunit interactions will down-modulate the catalytic activity. And accordingly, the recombinant of the invention can express a molecule which sterically hinders a naturally occurring enzyme or enzyme complex, so as to modulate biological functions.

Certain enzyme inhibitors afford good examples of functional down-modulation through covalent steric hindrance or modification. Suicide substrates which irreversibly bind to the active site of an enzyme at a catalytically important amino acid in the active site are examples of covalent modifications which sterically block the enzymatic active site. An example of a silicide substrate is TPCK for chymotrypsin (Fritsch, Enzyme Structure and Mechanism, 2d ed; Freeman & Co. Publishers, 1984)). This type of modulation is possible by the recombinant expressing a suitable silicide substrate, to thereby modulate biological responses (e.g., by limiting enzyme activity). There are also examples of non-covalent steric hindrance including many repressor molecules. The recombinant can express repressor molecules which are capable of sterically hindering and thus down-modulating the function of a DNA sequence-by preventing particular DNA-RNA polymerase interactions.

Allosteric effects are another way through which modulation is carried out in some biological systems. Aspartate transcarbamoylase is a well characterized allosteric enzyme. Interacting with the catalytic subunits are regulatory domains. Upon binding to CTP or UTP the regulatory subunits are capable of inducing a quaternary structural change in the holoenzyme causing down-modulation of catalytic activity. In contrast, binding of ATP to the regulatory subunits is capable of causing up-modulation of catalytic activity (Fritsch, supra). Using methods of the invention, molecules can be expressed which are capable of binding and causing modulatory quaternary or tertiary changes.

In addition, a variety of chemical modifications (e.g., phosphorylation, methylation, acetylation, adenylation, and uridenylation) may be carried out so as to modulate function. It is known that modifications such as these play important roles in the regulation of many important cellular components. Table 2 of Neidhardt, supra, at page 73, lists different bacterial enzymes which undergo such modifications. From that list, one skilled in the art can ascertain other enzymes of other systems which undergo the same or similar modifications, without undue experimentation. In addition, many proteins which are implicated in human disease also undergo such chemical modifications. For example, many oncogenes have been found to be modified by phosphorylation or to modify other proteins through phosphorylation or dephosphorylation. Therefore, the ability afforded by the invention to express modulators which can modify or alter function (e.g., phosphorylation) is of importance.

From the foregoing, the skilled artisan can use the CB4 vector to express a biological response modulator, without any undue experimentation.

With respect to expression of fusion proteins by inventive recombinants, reference is made to Sambrook, Fritsch, Maniatis, Molecular Cloning, A LABORATORY MANUAL (2nd Edition, Cold Spring Harbor Laboratory Press, 1989) (especially Volume 3), and Kendrew, supra, incorporated herein by reference. The teachings of Sambrook et al., can be suitably modified, without undue experimentation, from this disclosure, for the skilled artisan to generate recombinants or vectors expressing fusion proteins.

With regard to gene therapy and immunotherapy, reference is made to U.S. Pat. Nos. 4,690,915 and 5,252,479, which are incorporated herein by reference, together with the documents cited therein it and on their face, and to WO 94/16716 and U.S. Pat. No. 5,833,975 each of which is also incorporated herein by reference, together with the documents cited therein.

A growth factor can be defined as multifunctional, locally acting intercellular signaling peptides which control both ontogeny and maintenance of tissue and function (see Kendrew, supra, especially at page 455 et seq.). The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin (e.g., an interleukin selected from interleukins 1 to 14, or 1 to 11, or any combination thereof), macrophage colony stimulating factor, granulocyte colony stimulating factor, erythropoietin, mast cell growth factor, tumor suppressor p53, retinoblastoma, interferon, melanoma associated antigen or B7. U.S. Pat. No. 5,252,479 provides a list of proteins which can be expressed in an adenovirus system for gene therapy, and the skilled artisan is directed to that disclosure. WO 94/16716 and allowed U.S. Pat. No. 5,833,975, provide genes for cytokines and tumor associated antigens and immunotherapy methods, including ex vivo methods, and the skilled artisan is directed to those disclosures.

Thus, one skilled in the art can create a viral vector which expresses a growth factor or therapeutic gene and use the viral vector, from this disclosure and the knowledge in the art, without undue experimentation. Moreover, from the foregoing and the knowledge in the art, no undue experimentation is required for the skilled artisan to construct an viral vector which expresses an epitope of interest, a biological response modulator, a growth factor, a recognition sequence, a therapeutic gene, or a fusion protein; or for the skilled artisan to use such a viral vector.

As the viral vector of the present invention can be used for expression of gene products in vitro, techniques for protein purification can be employed in the practice of the invention, and such techniques, in general, include: Briefly, the cells are disrupted and the protein of interest is released into an aqueous "extract". There are many methods of cellular disintegration, which vary from relatively gentle to vigorous conditions, and the choice of one method over the other is dependent upon the source material. Animal tissues vary from the very easily broken erythrocytes to tough collagenous material such as found in blood vessels and other smooth-muscle containing tissue. Bacteria vary from fairly fragile organisms that can be broken up by digestive enzymes or osmotic shock to more resilient species with thick cell walls, needing vigorous mechanical treatment for disintegration. Gentle techniques include cell lysis, enzymatic digestion, chemical solubilization, hand homogenization and mincing (or grinding); moderate techniques of cell disintegration include blade homogenization and grinding with abrasive materials, i.e., sand or alumina; and vigorous techniques include french press, ultrasonication, bead mill or Manton-Gaulin homogenization. Each of the aforementioned techniques are art-recognized, and it is well within the scope of knowledge of the skilled artisan to determine the appropriate method of cell disintegration based upon the starting material, and the teachings herein and in the art. Following cell disintegration, the extract is prepared by centrifuging off insoluble material. At this stage, one may proceed with the purification method, as an extract containing as much of the protein of interest as possible has been prepared, and, where appropriate, particulate and most non-protein materials have been removed. Standard techniques of protein purification may be employed to further purify the protein of interest, including: precipitation by taking advantage of the solubility of the protein of interest at varying salt concentrations, precipitation with organic solvents, polymers and other materials, affinity precipitation and selective denaturation; column chromatography, including high performance liquid chromatography (HPLC, ion-exchange, affinity, immunoaffinity or dye-ligand chromatography; immunoprecipitation and the use of gel filtration, electrophoretic methods, ultrafiltration and isoelectric focusing. Each of the above-identified methods are well within the knowledge of the skilled artisan, and no undue experimentation is required to purify the proteins or epitopes of interest from expression of a recombinant or vector of the invention, using the standard methodologies outlined herein, and in the literature, as well as the teachings in the Examples below. Thus, the expression product generated by vectors or recombinants in this invention optionally can also be isolated and/or purified from infected or transfected cells; for instance, to prepare compositions for administration to patients. However, in certain instances, it may be advantageous to not isolate and/or purify an expression product from a cell; for instance, when the cell or portions thereof enhance the immunogenic effect.

As the expression products can provide an antigenic, immunological, or protective (vaccine) response, the invention further relates to products therefrom; namely, antibodies and uses thereof. More in particular, the expression products can elicit antibodies by administration of those products or of recombinants or vectors expressing the products. The antibodies can be monoclonal antibodies; and, the antibodies or expression products can be used in kits, assays, tests, and the like involving binding, so that the invention relates to these uses too. Additionally, since the recombinants or vectors of the invention can be used to replicate nucleic acid, the invention relates to the viral vectors and methods for replicating nucleic acid by infecting or transfecting cells with the recombinant and harvesting nucleic acid therefrom. The resultant nucleic acid can be used as probes or primers or for amplification.

The administration procedure for the viral vector, or expression products thereof, compositions of the invention such as immunological, antigenic or vaccine compositions or therapeutic compositions, can be via a parenteral route (intradermal, intramuscular or subcutaneous). Such an administration enables a systemic immune response. The administration can be via a mucosal route (e.g., oral, nasal, genital, etc.). Such administration generates a local immune response. More generally, the immunological or vaccine compositions or therapeutic compositions of the present invention can be prepared in accordance with standard techniques well known to those skilled in the pharmaceutical, medical or veterinary arts. Such compositions can be administered in dosages and by techniques well known to those skilled in the medical or veterinary arts taking into consideration such factors as the breed of species, age, sex, weight, and condition of the particular patient, and the route of administration. The compositions can be administered alone, or can be co-administered or sequentially administered with other compositions of the invention or with other immunological, antigenic or vaccine or therapeutic compositions. Such other compositions can include purified native antigens or epitopes or antigens or epitopes from expression by an inventive recombinant or vector or another vector system; and are administered taking into account the aforementioned factors.

Examples of compositions of the invention include liquid preparations for orifice (e.g., oral, nasal, anal, genital, such as vaginal, etc.) administration such as suspensions, syrups or elixirs; and, preparations for parenteral, subcutaneous, intradermal, intramuscular or intravenous administration (e.g., injectable administration) such as sterile suspensions or emulsions. In such compositions the viral vector may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. The standard texts incorporated herein by reference, may be consulted to prepare suitable preparations, without undue experimentation.

Compositions of the invention are conveniently provided as liquid preparations (e.g., isotonic aqueous solutions, suspensions, emulsions or viscous compositions) which may be buffered to a selected pH. If digestive tract absorption is preferred, compositions of the invention can be in the "solid" form of pills, tablets, capsules, caplets and the like, including "solid" preparations which are time-released or which have a liquid filling (e.g., gelatin covered liquid, whereby the gelatin is dissolved in the stomach for delivery to the gut). If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size. Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, such as liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the immunogen, and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Viscous compositions are normally prepared from solutions by the addition of such thickening agents.

A pharmaceutically acceptable preservative can be employed to increase the shelf-life of the compositions of the present invention. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the viral vector and/or immunogen or epitope or fragment expressed therefrom and optional additional adjuvant. This will present no problem to those skilled in chemical and pharmaceutical principles, or problems can be readily avoided by reference to standard texts or by simple experiments (not involving undue experimentation), from this disclosure and the documents cited herein.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other mammals can be determined without undue experimentation by the skilled artisan, from this disclosure, the documents cited herein, the Examples below (e.g., from the Examples involving mice and from the applications cited herein).

Suitable regimes for initial administration and booster doses or for sequential administrations also are variable, may include an initial administration followed by subsequent administrations; but nonetheless, may be ascertained by the skilled artisan, from this disclosure, the documents cited herein, including applications cited herein, and the Examples below. The compositions can be administered alone, or can be co-administered or sequentially administered with other compositions of the invention or with other prophylactic or therapeutic compositions. A subject can be treated or administered in accordance with the present invention by administering the vector suspended in or admixed with a physiologically suitable excipient. The vector or an immunogen or epitope or fragment thereof, can be administered in any suitable amount to achieve expression at a suitable dosage level.

Antigenic, immunological or vaccine compositions typically can contain an adjuvant and an amount of the recombinant or vector or expression product to elicit the desired response. In human applications, alum (aluminum phosphate and/or aluminum hydroxide) is a typical adjuvant. Saponin and its purified component Quil A, Freund's complete adjuvant and other adjuvants used in research and veterinary applications have toxicities which limit their potential use in human vaccines; see also PCT/US/98/23472 with respect to adjuvants that can be used in the practice of this invention. Chemically defined preparations such as muramyl dipeptide, monophosphoryl lipid A, phospholipid conjugates such as those described by Goodman-Snitkoff et al., *J. Immunol.* 147: 410-415 (1991) and incorporated by reference herein, encapsulation of the protein within a proteoliposome as described by Miller et al., *J. Exp. Med.* 176: 1739-1744 (1992) and incorporated by reference herein, and encapsulation of the protein in lipid vesicles such as Novasome™ lipid vesicles (Micro Vescular Systems, Inc., Nashua, N.H.) can also be used.

The composition may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, and the like administration. And again, the effective dosage and route of administration are determined by the nature of the composition, by the nature of the expression product, by expression level if the vector is directly used, and by known factors, such as breed or species, age, sex, weight, condition and nature of host, as well as $LD_{50}$ and other screening procedures which are known and do not require undue experimentation. Dosages of expressed product (e.g., HIV p24) can range from a few to a few hundred micrograms (e.g., 5 to 500 μg). The viral vector can be administered in any suitable amount to achieve expression at these dosage levels. The viral vector can be administered in an amount of about $10^{3.5}$ pfu; thus, the viral vector is preferably administered in at least this amount; more preferably about $10^4$ pfu to about $10^6$ pfu; however higher dosages such as about $10^4$ pfu to about $10^{10}$ pfu (e.g., about $10^5$ pfu to about $10^9$ pfu) for instance about $10^6$ pfu to about $10^8$ pfu can be employed. Reference is also made to the Examples herein, as well as documents cited herein. Other suitable carriers or diluents can be water or a buffered saline, with or without a preservative. The viral vector or the expression product thereof may be lyophilized for resuspension at the time of administration or can be in solution. Typically, an adjuvant is commonly used as 0.001 to 50 wt % solution in phosphate buffered saline, and the immunogen is present on the order of micrograms to milligrams, such as about 0.0001 to about 5 wt %, preferably about 0.0001 to about 1 wt %, most preferably about 0.0001 to about 0.05 wt % (see, e.g., in applications and references cited herein). Typically, however, the immunogen is present in an amount on the order of micrograms to milligrams, or, about 0.001 to about 20 wt %, preferably about 0.01 to about 10 wt %, and most preferably about 0.05 to about 5 wt %. Of course, for any composition to be administered to an animal or human, including the components thereof, and for any particular method of administration, it is preferred to determine therefor: toxicity, such as by determining the lethal dose (LD) and LD50 in a suitable animal model e.g., rodent such as mouse; and, the dosage of the composition(s), concentration of components therein and timing of administering the composition(s), which elicit a suitable immunological response, such as by titrations of sera and analysis thereof for antibodies or immunogens (e.g., by ELISA analysis). Such determinations do not require undue experimentation from the knowledge of the skilled artisan, this disclosure and the documents cited herein. And, the time for sequential administrations can be ascertained without undue experimentation. Standard texts, such as Remington: The Science and Practice of Pharmacy, 17th edition, Mack Publishing Company, incorporated herein by reference, can be consulted to prepare suitable compositions and formulations for administration, without undue experimentation. Suitable dosages can also be based upon the text and documents cited herein. A determination of the appropriate dosages is thus within the skill of one in the art given the parameters herein.

The carrier may also be a polymeric delayed release system. Synthetic polymers are particularly useful in the formulation of a composition having controlled release. An early example of this was the polymerization of methyl methacrylate into spheres having diameters less than one, micron to form so-called nano particles, reported by Kreuter, J., Microcapsules and Nanoparticles in Medicine and Pharmacology, M. Donbrow (Ed). CRC Press, p. 125-148.

Microencapsulation has been applied to the injection of micro encapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d, 1-lactide-co-glycolide) (PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al. Current Topics in Microbiology and Immunology 1989, 146:59-66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A nonsolvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction. Thus, solid, including solid-containing-liquid, liquid, and gel (including "gel caps") compositions are envisioned.

Furthermore, the viral vector can be used in any desired immunization or administration regimen (e.g., as part of periodic vaccinations such as annual vaccinations) as in the veterinary arts or as in periodic vaccinations as in the human medical arts, or as in a prime-boost regimen wherein an inventive vector or recombinant is administered either before or after the administration of the same or of a different epitope of interest or recombinant or vector expressing such a same or different epitope of interest (including an inventive recombinant or vector expressing such a same or different epitope of interest).

Additionally, the viral vector or the expression products therefrom can stimulate an immune or antibody response in animals. From those antibodies, by techniques well-known in the art, monoclonal antibodies can be prepared and, those monoclonal antibodies, can be employed in well known antibody binding assays, diagnostic kits or tests to determine the presence or absence of antigen(s) and therefrom the presence or absence of the natural causative agent of the antigen or, to determine whether an immune response to that agent or to the antigen(s) has simply been stimulated. Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, (e.g., Koprowski, H. et al., U.S. Pat. No. 4,196,265, issued Apr. 1, 1989). Uses of monoclonal antibodies are known. One such use is in diagnostic methods (David, G. and Greene, H., U.S. Pat. No. 4,376,110, issued Mar. 8, 1983). Monoclonal antibodies have also been used to recover materials by immunoadsorption chromatography (Milstein, C., 1980, Scientific American 243:66, 70).

Furthermore, the viral vector or expression products therefrom can be used to stimulate a response in cells in vitro or ex vivo for subsequent reinfusion into a patient. If the patient is seronegative, the reinfusion is to stimulate an immune response (e.g., an immunological or antigenic response such as active immunization). In a seropositive individual, the reinfusion is to stimulate or boost the immune system against a pathogen.

The recombinants or vectors of the invention are also useful for generating nucleic acids for probes or for PCR primers which can be used to detect the presence or absence of hybridizable DNA or RNA or to amplify DNA or RNA, (e.g., to detect a pathogen in a sample).

Furthermore, the viral vector of the present invention can be generated and employed in a manner analogous to the methods for making and/or using and/or administering a vector, either in vivo or in vitro, see e.g., U.S. Pat. Nos. 4,603,112, 4,769,330, 5,174,993, 5,505,941, 5,338,683, 5,494,807, 4,722,848, 5,942,335, 5,364,773, 5,762,938, 5,770,212, 5,942,235, 5,756,103, 5,766,599, 6,004,777, 5,990,091, 6,033,904, 5,869,312, 5,382,425, WO 94/16716, WO 96/39491, Paoletti, "Applications of pox virus vectors to vaccination: An update," PNAS USA 93: 11349-11353, October 1996, Moss, "Genetically engineered poxviruses for recombinant gene expression, vaccination, and safety," PNAS USA 93: 11341-11348, October 1996, Smith et al., U.S. Pat. No. 4,745,051, Richardson, C. D. (Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, Dec., 1983, Vol. 3, No. 12, p. 2156-2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399-406; EPA 0 370 573, U.S. application Ser. No. 920,197, filed Oct. 16, 1986, EP Patent publication No. 265785, U.S. Pat. No. 4,769,331, Roizman, "The function of herpes simplex virus genes: A primer for genetic engineering of novel vectors," PNAS USA 93: 11307-11312, October 1996, Andreansky et al., "The application of genetically engineered herpes simplex viruses to the treatment of experimental brain tumors," PNAS USA 93:11313-11318, October 1996, Robertson et al. "Epstein-Barr virus vectors for gene delivery to B lymphocytes," PNAS USA 93:11334-11340, October 1996, Frolov et al., "Alphavirus-based expression vectors: Strategies and applications," PNAS USA 93:11371-11377, October 1996, Kitson et al., J. Virol. 65, 3068-3075, 1991; U.S. Pat. Nos. 5,591,439, 5,552,143, Grunhaus et al., 1992, "Adenovirus as cloning vectors," Seminars in Virology (Vol. 3) p. 237-52, 1993, Ballay et al., EMBO Journal, vol. 4, p. 3861-65, Graham, Tibtech 8, 85-87, April, 1990, Prevec et al., J. Gen Virol. 70, 429-434, PCT W091/11525, Felgner et al. (1994), J. Biol. Chem. 269, 2550-2561, Science, 259:1745-49, 1993 and McClements et al., "Immunization with DNA vaccines encoding glycoprotein D or glycoprotein B, alone or in combination, induces protective immunity in animal models of herpes simplex virus-2 disease," PNAS USA 93:11414-11420, October 1996, and U.S. Pat. Nos. 5,591,639, 5,589,466, and 5,580,859; WO 98/33510; Ju et al., Diabetologia, 41:736-739, 1998; Sanford et al., U.S. Pat. No. 4,945,050; Fischbach et al. (Intracel), WO 90/01543; Robinson et al., seminars in IMMUNOLOGY, vol. 9, pp. 271-283 (1997); Szoka et al., U.S. Pat. No. 4,394,448; and McCormick et al., U.S. Pat. No. 5,677,178; Sambrook, Fritsch and Maniatis, Molecular Cloning, A Laboratory Manual, 2nd Ed., Cold Spring Harbor Laboratory Press, 1982 (e.g., procedures for producing heterologous peptides and methods of isolating and purifying heterologous peptides). Generally, recombinant DNA technology has enabled the expression of foreign (heterologous) proteins in microbial and other host cells. In this process, a vector containing genetic material directing a host cell to produce a protein encoded by a portion of a heterologous DNA sequence is introduced into the host, and the transformed host cells can be fermented and subjected to conditions which facilitate the expression of the heterologous DNA, leading to the formation of large quantities of the desired protein. Plasmids are extensively used as vectors to clone DNA molecules. Most plasmid vectors are made by taking DNA from a variety of replicons (plasmids, bacteriophage chromosomes and bacterial chromosomes) and joining the DNA together (using restriction enzymes and DNA ligase) to form a plasmid which has an origin of replication, a selection marker (usually an antibiotic-resistance gene) and a promoter for expressing genes of interest in the required host cell.

In the present invention, exogenous or heterologous or foreign DNA, e.g., encoding an immunogen(s) or epitope(s) or a fragment(s) is inserted into a plasmid vector encoding the genome of the attenuated B4 coxsackievirus. The sequence (e.g., coding sequence) to be expressed, is advantageously inserted in the correct relationship to a host-specific promoter and other transcriptional regulatory sequences and advantageously in the correct reading frame, so that the heterologous peptide is produced. Even more advantageously, the heterologous or foreign or exogenous sequence is inserted within the immunogenic coat region of the genome. The plasmid vector also can also contain sequences for efficient transcription or translation (e.g., the Shine-Dalgamo Region for expression in bacterial cells, the Internal Ribosomal Entry Site (IRES) for efficient translation of a bicistronic message, promoter enhancer sequences to modulate expression levels and/or direct expression within a particular cell type). Plasmid vectors can contain a transcription termination site 3' to the inserted gene(s) to ensure the mRNA produced avoids run on through the vector.

The present invention further relates to a composition containing an inventive coxsackievirus and/or foreign peptide or protein expressed from the coxsackievirus, e.g., antigen or antigens or immunogen or immunogens or epitope or epitopes from expression of the inventive coxsackievirus, e.g. coxsackievirus CB4-P coat protein and/or HIV p24 immunogen(s) and/or epitope(s) thereof. The inventive coxsackievirus B4-P variant vector can contain exogenous or heterogolous or foreign DNA, advantageously encoding any desired peptide or protein fragment or thereof, such as an antigen or immunogen or epitope. The composition or vector can induce in a subject an immunogenic or immunological or therapeutic response; advantageously, the response is protective, e.g., against coxsackievirus pathogenesis, and/or the response is an immunogenic B and/or T cell response. The response can be synergistic or improved in comparison with previous vectors or compositions.

The invention further relates to a method of inducing in a subject an immunogenic response that is protective against coxsackievirus pathogenesis. This response can be synergistic or improved in comparison with previous compositions or vectors. For the purposes of this invention, an immunogenic response that is protective against coxsackievirus pathogenesis can be, for example, directed to treatment, prevention or delaying myocarditis, myositis or pancreatic disease such as pancreatitis or diabetes mellitus, e.g., insulin-dependent diabetes (IDDM, Type I) or juvenile diabetes The therapeutic response can be, but does not have to be, the result of the activity of a medicament or of a gene therapy or activation approach where, a foreign or heterologous sequence is introduced or delivered, e.g., in vitro into the cells or in vivo, via a coxsackieviral vector to provide expression of a desired gene or the induction thereof. Gene activation can be the introduction into a cell of an ectopic copy of the gene under the control of an appropriate regulatory element or the activation of the endogenous gene within the cell.

In a preferred embodiment, the invention further relates to a CB4 vector which expresses an HIV polypeptide or a fragment thereof, and also to expression products thereof, immunological, immunogenic or vaccine compositions therefrom, (e.g., subunit and/or multivalent vaccine compositions comprising of HIV and/or coxsackievirus epitopic region(s), and/or polypeptide(s) and/or fragment(s), such as coxsackievirus CB4-P coat protein and/or HIV p24). Such viral vectors or compositions can be useful in the treatment and/or prevention of HIV. Advantageously, the viral vector or composition containing said viral vector can provide immunogenic or immunological responses against HIV. It is desired that these responses approach or achieve a protective immune response and/or are improved in comparison with prior compositions or vectors and/or exhibit synergy.

Such a viral vector is administered to infected individuals, (e.g., seropositive individuals) to augment the immune response in a subject to the virus. Such a viral vector can also serve as a vaccine, and is administered to uninfected individuals to stimulate an immune response in a subject which is protective against the virus. The response can be improved or synergistic with respect to prior immunological or immunogenic compositions against HIV or an immunodeficiency virus because the antigen or epitope expressed in vivo or in vitro can include a T-cell activator such as a coxsackievirus coat protein (e.g., the CB4-P VP1 capsid protein). The viral vector can comprise a subunit of one or more HIV and/or HIV/CB4-P fusion proteins or fragments thereof, such as a HIV p24 or a fragment thereof. A vaccine composition made from the viral vector of the present invention can be multivalent, wherein the composition contains at least two epitopes-having different amino acid sequences.

The present invention is additionally described by way of the following illustrative, non-limiting Examples, that provide a better understanding of the present invention and of its many advantages.

EXEMPLIFICATION

Example 1

CB4-P Variant as a Vector that can Express Peptides.

This Example shows that (a) a CB4-P variant can be used as a vector for expressing short peptides within a capsid protein and (b) a recombinant CB4-P variant can induce a CD4+ T cell response against the foreign sequence. Therefore, CB4-P can be used as an expression vector and insertion of heterologous peptides into an immunogenic region is a viable strategy for inducing T helper cell responses against the foreign sequence.

While the three-dimensional structure of coxsackievirus B3 has been solved (Muckelbauer et al., *Structure* 3: 653-667 (1995)), the antigenic structure of the group B viruses has not been well characterized. The high degree of sequence identity (72%) between the VP1 capsid proteins of B3 and B4 allows a prediction of the structure of VP1 of coxsackievirus B4 based on a sequence-structure alignment (Halim and Ramsingh, *Virol.* 269: 86-94 (1999)). A major neutralization antigenic site, possibly analogous to site I of poliovirus, has been mapped to the predicted BC-loop of VP1 of coxsackievirus B4 (Halim and Ramsingh, *Virol.* 269: 86-94 (1999)). In addition, the DE-loop of VP1 is within a conformational B-cell epitope, possibly analogous to the neutralization antigenic site 1B of poliovirus.

To determine if the DE-loop of VP1 also contains a T helper cell epitope, CD4+ T cells from the spleens of mice infected with CB4-P were tested in a proliferation assay. Briefly, viral infectivity was assessed by plaque assay with LLC-MK2(D) cells. The passage histories of the two viral variants, CB4-P and CB4-V, have been described (Ramsingh et al., *J. Virol.* 71(11): 8690-7 (1997)). Large scale stocks of CB4-P and CB4-V were prepared in HeLa cells and LLC-MK2(D) cells, respectively. Viral infectivity was assessed by plaque assay with LLC-MK2(D) cells. Two strains of mice were used; the B10.S(12R) mice are maintained in a research laboratory and the BALB/c mice are bred in the Health Research Institute's Animal Core Facility. Mice were injected intraperitoneally with $10^4$ pfu of virus and monitored daily. Mice were sacrificed at various times after infection and pancreases and spleens were harvested. All animal procedures were approved by the Institutional Animal Care and Use Committee of the Wadsworth Center.

The proliferation assay was carried out against a peptide, 122P, spanning residues 122 to 136 of VP1. This peptide contains all but four residues of the DE-loop of VP1. CD4+ T cells from the spleens of infected mice proliferated in response to peptide 122P (FIG. 1A).

The DE-loop of VP1 of CB4-P was chosen as the site for insertion of foreign sequences since the loop is immunogenic, containing both T and B cell epitopes (FIG. 1C), and is long, flexible and not highly conserved among the group B viruses (Muckelbauer et al., *Structure* 3: 653-667 (1995); Halim and Ramsingh, *Virol.* 269: 86-94 (1999)).

Figure 2:
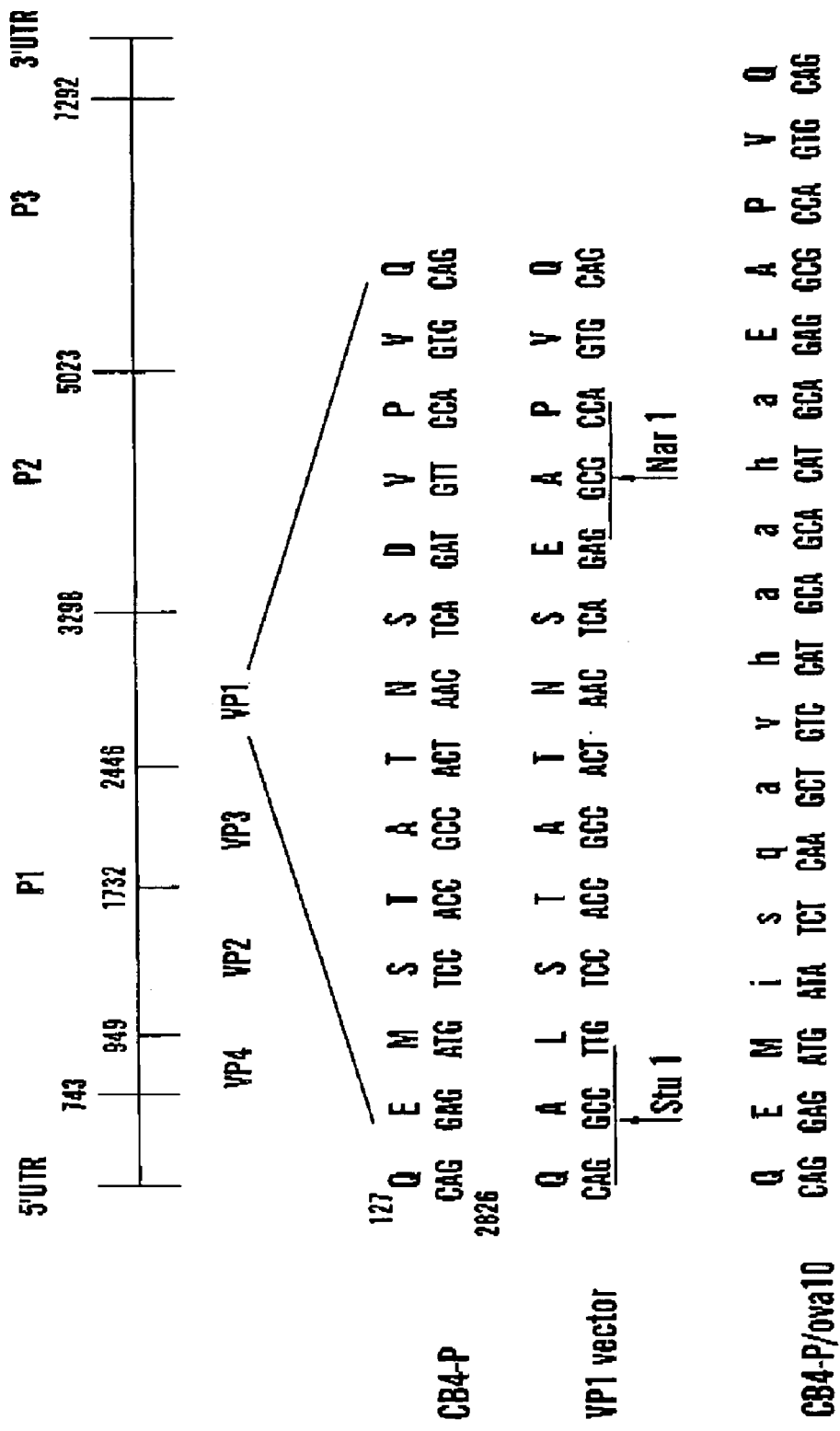
FIG. 2 (SEQ ID NOS: 15-20) shows a recombinant, chimeric coxsackievirus containing ten amino acids of ovalbumin sequence is genetically stable after multiple passages in cell culture. The top line shows a schematic representation of the structural organization of the coxsackievirus B4 (JVB strain) genome. The predicted DE-loops of VP1 of CB4-P and the cassette vector, spanning amino acid residues 128 to 140, are shown. The VP1 vector was constructed by introducing two unique restriction enzyme sites (StuI, NarI) into a full-length infectious cDNA clone of CB4-P which resulted in four amino acid substitutions (shown in bold). After six passages in LLC-MK2(D) cells, the genetic stability of CB4-P/ova10 was assessed by sequence analysis.

The VP1 expression vector was constructed by inserting two unique restriction enzyme sites (StuI, NarI) into a full-length infectious cDNA clone of CB4-P which has been described (Caggana et al., *J. Virol.* 67: 4797-803 (1993)) (FIG. 2). Mutagenesis was accomplished using a recombinant PCR strategy. StuI and NarI sites were created in two overlapping viral cDNA fragments at nucleotide positions 2827-2832 and 2855-2860, respectively. The two overlapping PCR products were denatured, allowed to anneal, and amplified in a third PCR using two internal primers. The resulting fragment was cloned into a full-length cDNA of CB4-P to generate the cassette vector. Clones were screened initially by restriction enzyme analysis followed by DNA sequence analysis. Clones were sequenced in both the forward and reverse orientation by the dideoxy chain-termination method using an automated DNA sequencer (Applied Biosystems 373A or 377). At least 250 bp of sequence, flanking the site of interest, was analyzed. In addition, all recombinant viruses were subjected to RNA sequence analysis. Briefly, monolayers of LLC-MK2(D) cells were infected at a multiplicity of infection of 0.2 pfu per cell. Total cellular RNA was extracted by using Ultraspec (BioTecx) at 24 h post infection. After reverse transcription using random primers, specific regions of the viral cDNA were amplified by PCR and sequenced.

Introduction of the two cloning sites resulted in four amino acid substitutions. A methionine residue at position 129 of VP1 of coxsackievirus B4 was shown to be an attenuating determinant while a threonine residue at the same position was shown to be a major determinant of virulence (Caggana et al., *J. Virol.* 67: 4797-803 (1993)). In the cassette vector, met-129 is replaced by a leucine residue by the insertion of the StuI site. To maintain the phenotype of the avirulent, parental virus, leu-129 of VP1 within the cassette vector was replaced with met-129 in the recombinants. The resulting clones lost the StuI site and regained a glutamic acid and a methionine residue at positions 128 and 129, respectively, of VP1.

An immunogenic ovalbumin peptide, OVA 323-339 which is I-A$^d$ restricted (Murphy et al., *Science* 250: 1720-1723 (1990)), was used as a test sequence for insertion into the CB4-P expression vector. Ovalbumin sequences representing successive COOH-terminal truncations of the OVA 323-339 peptide were cloned into the CB4-P cassette vector. Oligonucleotides encoding six to sixteen amino acids of ovalbumin sequence were inserted into the CB4-P cassette vector in order to construct chimeric viruses. To retain two viral amino acids at positions 128 and 129 of VP1, and to maintain the correct reading frame, oliogonucleotide sequences began with AGATG and ended with GAGG. Oliogonucleotide sequences plus their complements were synthesized by the Molecular Genetics Core Facility. Oliogonucleotide pairs were annealed after boiling at 950 C for 5 minutes followed by incubation at 55° C. for 10 minutes. Sequences were cloned, using standard methodologies, into the CB4-P cassette vector after digestion with StuI and NarI. Recombinants were screened initially by restriction enzyme analysis. Clones were identified based on the loss of the StuI site with retention of the NarI site. Clones were verified by DNA sequencing.

Recombinant viruses were obtained by transfecting LLC-MK2(D) cells with in vitro-derived RNA transcripts as described (Caggana et al., *J. Virol.* 67: 4797-803 (1993)). Briefly, after linearization of recombinant cDNAs with Sac1, T3 RNA polymerase was used to make plus-sense viral RNA transcripts. Transfection was accomplished by electroporation, Viral RNA transcripts (25-35 μg) were added to LLC-MK2(D) cells (2×10$^6$), which were resuspended in PBS lacking calcium and magnesium. Cells were shocked twice at 0.8 kv (BiolRad GenePulser) and plated, in duplicate, in 60 mm plates containing DMEM plus 5% fetal calf serum. Virus was harvested when cells exhibited 80 to 100% CPE. After plaque purification, viral stocks were grown in LLC-MK2(D) cells.

Viral replication was analyzed under single-step conditions. LLC-MK2(D) cells were infected at a multiplicity of infection of 2-5 pfu per cell. After an adsorption period of 30 min. at 25°, the unadsorbed inoculum was removed and the monolayer was washed three times with phosphate-buffered saline. virus was harvested after repeated freezing and thawing of infected cells. Viral infectivity was determined by plaque assay.

Viral replication in B10 mice has been studied extensively (Ramsingh et al., *Virus Res.* 14: 347-58 (1989); Ramsingh et al., *J. Virol.* 71(11): 8690-7 (1997)). Replication of the chimeric viruses was analyzed in B10.S(12R) mice. Mice were infected as described above. At various times after infection, pancreatic tissue homogenates were prepared and assayed for infectivity by plaque assay as previously described (Ramsingh et al., *J. Virol.* 71(11): 8690-7 (1997)).

Viability of the chimeric viruses was dependent on the size of the inserted sequence. Of 4 CB4-P/ova chimeric cDNAs, viable virus was obtained from 2 constructs containing six (323-328) and ten (323-332) amino acids of ovalbumin sequence (CB4-P/ova6, CB4-P/ova10) (Table 1).

TABLE I

Summary of viability and genetic stability of recombinant, chimeric coxsackieviruses
(SEQ ID NOS: 4-7, respectively in order of appearance).

| Virus | Inserted Sequence | Viability | Retention of insert |
|---|---|---|---|
| CB4-P/ova6 | ISQAVH | + | No |
| CB4P/ova10 | ISQAVHAAHA | + | Yes |
| CB4P/ova14 | ISQAVHAAHAEINE | − | |
| CB4P/ova16 | ISQAVHAAHAEINEAG | − | |

Insertions of 14 and 16 amino acids did not yield viable viruses. The genetic stability of CB4-P/ova6 and CB4-P/ova10 was assessed by sequencing viral genomic RNA after multiple rounds of replication. After two passages in cell culture, the CB4-P/ova6 recombinant had lost its inserted sequence. The CB4-P/ova10 recombinant, however, was genetically stable since it retained the ovalbumin sequence after six passages in cell culture (FIG. 2). At least 250 bp of sequence on either side of the insertion site was analyzed and mutations were not observed in the surrounding sequences for either CB4-P/ova6 or CB4-P/ova10. The CB4-P/ova10 recombinant was also grown in mice. Virus was harvested from the pancreatic tissues of infected mice, amplified in cell culture and assessed for genetic stability. The recombinant retained the inserted sequence after replication in cell culture and in mice.

Structural analysis suggests that the DE-loop of VP1 of coxsackievirus B3 plays a role in the physical stability of the virion (Muckelbauer et al., *Structure* 3: 653-667 (1995)). Disruption of this loop may alter viral stability and hence viral replication. The physical stability of the recombinant was assessed by thermal inactivation. At 44° C., the CB4-P variant was more thermostable than a virulent variant, CB4-V. The kinetics of inactivation of CB4-P/ova 10 were similar to that of the more thermostable virus, CB4-P (FIG. 3).

Figure 4A:
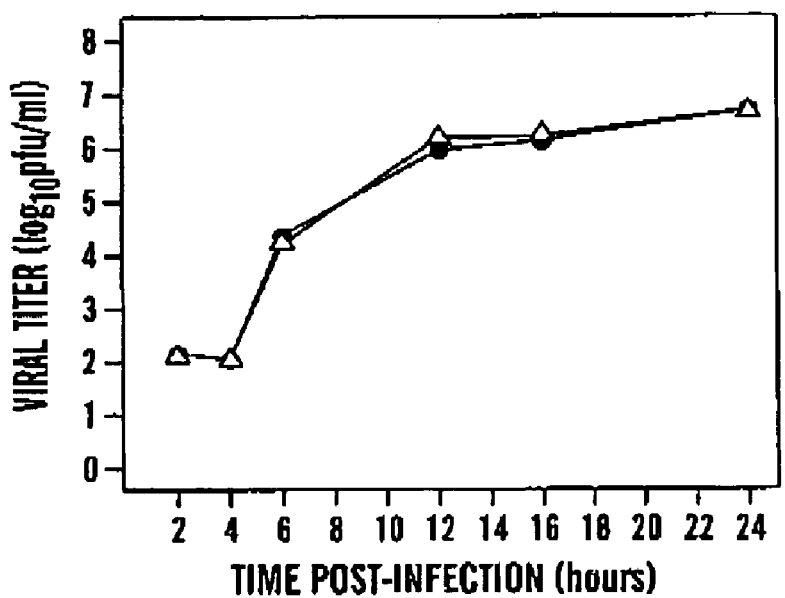
Figure 4B:
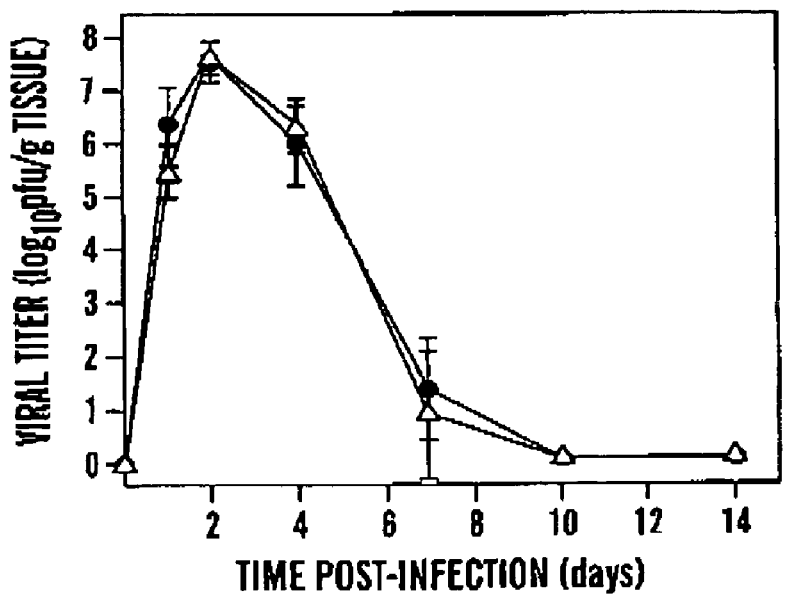

To determine if the insertion of heterologous sequences into the VP1 capsid protein of CB4-P affected replication, the growth kinetics of the recombinant was analyzed in cell culture and in mice. The kinetics of replication of CB4-P/ova10 in cell culture were similar to that of CB4-P under single-step conditions (FIG. 4A). Previous studies have shown that the pancreas is a major site of replication for CB4-P which induces a transient pancreatitis (inflammation of the exocrine pancreas) (Caggana et al., *J. Virol.* 67: 4797-803 (1993); Ramsingh et al., *J. Virol.* 71(11): 8690-7 (1997)). The kinetics of viral replication in the pancreatic tissues of mice infected with CB4-P/ova10 were similar to that observed with CB4-P (FIG. 4B). Viral titers peaked two days after infection. Infectious virus was no longer detected ten days after infection.

Previous studies showed the DE loop of VP1 of coxsackievirus B4 to have an influence on virulence (Caggana et al., *J. Virol.* 67: 4797-803 (1993)). To test whether disruption of the DE loop affected pathogenicity, mice were infected with the chimeric virus. Male BALB/c mice were used since they succumb to infection with the virulent variant, CB4-V, but survive infection with CB4-P (Ramsingh et al., *J. Virol.* 73:(4) 3080-3086 (1999)). Mice survived infection with CB4-P/ova10. During the four week follow-up, infected mice were well-groomed and appeared healthy.

The ten amino acids of ovalbumin sequence expressed within CB4-P/ova10 contained the core sequence (SEQ ID NO: 8) ($^{327}$VHAAHA$^{332}$) that is critical for binding of the ovalbumin peptide to the MHC class II molecule, I-A$^d$ (Hunt et al., *Science* 256: 1817-1820 (1992)). In order to determine whether the ovalbumin sequence within the recombinant was able to elicit a T helper cell response, a proliferation assay was carried out using infected BALB/c (H-2$^d$) mice. BALB/c mice were injected intraperitoneally with 10$^4$ pfu of CB4-P/ova10 or CB4-P. Spleens were harvested two weeks later. Briefly, red blood cells were removed from spleen cell suspensions by hypotonic lysis in 0.15 M ammonium chloride. B cells were removed by magnetic separation after incubation with rabbit-anti-mouse Ig and goat-anti-rabbit IgG coated magnetic beads (Advanced Magnetics, Cambridge, Mass.). Residual B cells, macrophages, and CD8+ T cells were lysed after incubation with monoclonal antibodies (J11D, M1/70, anti-lyt2) and complement. The purification protocol yielded a CD4+ T cell preparation that was 50-75% pure. Antigen presenting cells (APC), consisting primarily of B cells and macrophages, were purified from the spleens of uninfected BALB/c mice by negative selection (Coligan et al., Current Protocols in Immunology. New York: John Wiley & Sons, 1996). Red blood cells were removed from spleen cell suspensions by hypotonic lysis. T cells were lysed after incubation with anti-thyl.2 and complement. To prevent proliferation, the APC (macrophages and B cells) were treated with mitomycin C (25 μg/ml) for 20 minutes at 37°. The CD4+ T cells (2×10$^5$) and APC (2×10$^5$) were cultured in the presence of peptide (0-5 μg/well) or 5×10$^4$ pfu of heat-inactivated virus (56° for 1 hour), in 96-well round bottom plates (Corning). (Peptides were synthesized by the Peptide Synthesis Core Facility using an Applied Biosystems 431A or 432A peptide synthesizer). After 4 days, cells were pulsed with 1 μCi of [$^3$H] methylthymidine (5 Ci/mmol) per well for 17 hours. Cells were harvested and lysed using an automatic cell harvester (Tomtec Cell Harvester 96). [$^3$H] thymidine incorporation was used as the indicator of CD4+ T cell activation.

CD4+ T cells recognize peptide fragments of 13 to 17 amino acids (Janeway and Travers, Immunobiology: The Immune System in Health and Disease. Third ed. London, New York: Current Biology Ltd./Garland Publishing Inc. 1997). Since 10 amino acids of ovalbumin sequence are present within the recombinant virus, we examined T cell proliferation against a chimeric peptide, ova/virus14, containing ten amino acids of ovalbumin sequence and four amino acids of viral sequence. T cell proliferation against the original 17-amino acid ovalbumin peptide, OVA 323-339 was also tested. T cells from CB4-P/ova10 infected mice proliferated in response to both the chimeric ova/virus14 peptide and the OVA 323-339 peptide, but not to an unrelated peptide (FIG. 5). T cells from uninfected mice or mice infected with the CB4-P parental strain did not proliferate in response to the chimeric ova/virusl4 peptide, the OVA 323-339 peptide or an unrelated peptide (FIG. 5).

EXAMPLE 2

Eliciting CTL and CD4+ T Helper Cell Responses.

Figure 6A:
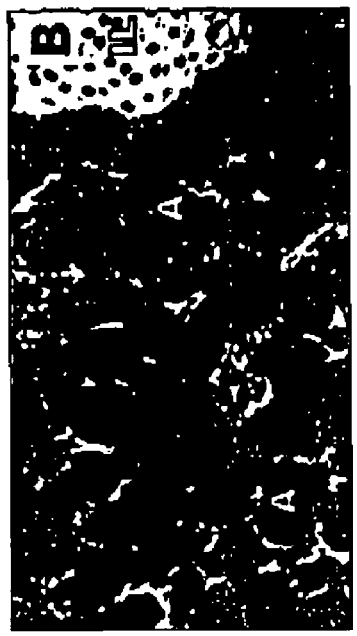
Figure 6B:
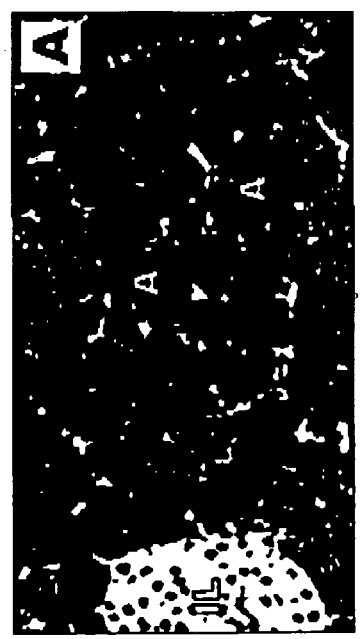
Figure 6C:
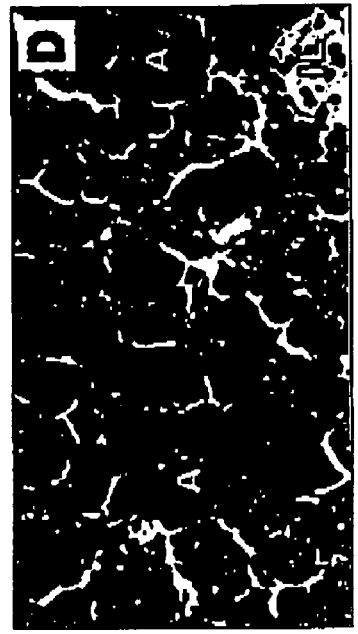
Figure 6D:
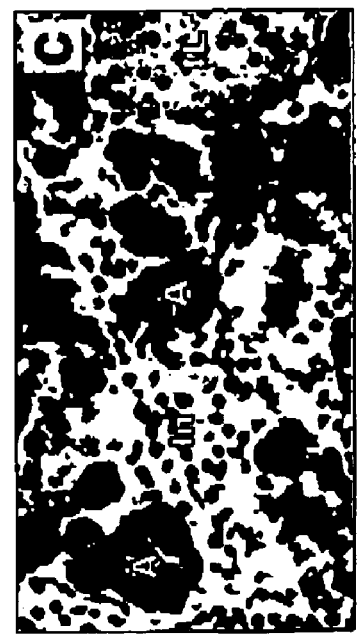

Two strategies designed to elicit CTL and CD4+ T helper cell responses were used to construct CB4-P/HIV gag p24 recombinants. In one design, gag p24 peptides were expressed within a surface loop of the VP1 capsid protein (Halim et al., *Vaccine* 19: 958-965 (2001)). To elicit a CTL response, the foreign peptide need not be present within the recombinant. In the second design, gag p24 sequences were expressed at the amino-terminus of the CB4-P polyprotein. Recombinant viruses were viable, genetically stable, and retained the avirulent phenotype of the parental virus.

Interference with administration of the recombinant virus due to pre-existing immunity to the vector did not occur. Prior exposure to the parental CB4-P virus did not affect the ability of the recombinant to induce a CD4+ T cell response against the foreign sequence. The CB4-P/ova10 chimera was able to elicit a CD4+ T cell response against ovalbumin sequences. In addition, the recombinant virus is capable of inducing a CD4+ T cell response against ovalbumin sequences in mice that had been previously infected with the CB4-P parental virus.

The attenuated CB4-P variant has been characterized extensively in immunocompetent strains of mice, SJL, B10, and BALB/c (Ramsingh et al., *Virus Res.* 14: 347-58 (1989); Caggana et al., *J. Virol.* 67: 4797-803 (1993); Ramsingh et al., *J. Virol.* 71(11): 8690-7 (1997)). CB4-P induces a mild, transient inflammation of the pancreas which is followed by repair of the damaged tissues (Chapman et al., *Curr. Topics Microbiol. Immunol.:* 223227-58 (1997)). Viral titers peak in pancreatic tissues two days after infection. Infectious virus is cleared within seven-to-ten days of infection (Ramsingh et al., *J. Virol.* 71(11): 8690-7 (1997)). Infected mice appear healthy and are well-groomed.

The molecular basis of attenuation has been determined using a panel of recombinant, chimeric viruses constructed from the avirulent CB4-P variant and a closely related variant, CB4-V, which is virulent (Caggana et al., *J. Virol.* 67: 4797-803 (1993); Ramsingh et al., *Virus Res.* 23: 281-92 (1992)). Depending on the mouse strain, CB4-V infection can be lethal (Janeway and Travers, Immunobiology: The Immune System in Health and Disease. Third ed. London, New York: Current Biology Ltd./Garland Publishing Inc. 1997). To determine if CB4-P retained its avirulent phenotype in immunodeficient mice, mice lacking CD4+ T cells (CD4 ko), IL-4 (IL-4 ko), or γ-interferon (γ-IFN ko) as well as mice with a restricted T cell repertoire (D011.10) were infected and monitored for four weeks (Murphy et al., *Science:* 2501720-3 (1990)). Several strains of mice were used; the three B 10H-2 congenic strains, B10.S(12R), B10.T(6R), and B10.Q, are maintained in a research laboratory facility, the BALB/c mice are bred in the Health Research Institute's Animal Core Facility and the knockout (ko) and transgenic lines are maintained by Dr. William Lee at the Wadsworth Center. All of the ko strains, CD4 ko, IL-4 ko, and γ-interferon ko, and the transgenic line, D011.10, are on a BALB/c genetic background (Murphy et al., *Science:* 2501720-3 (1990); Killeen et al., *EMBO J.:* 121547-53 (1993); Noben-Trauth et al., *Science:* 271987-90 (1996); Dalton et al., *Science:* 2591739-45 (1993)). Most of the CD4+ T cells of the D011.10 strain express a T-cell receptor that recognizes an ovalbumin peptide, OVA 323-339. All infected mice appeared healthy and survived infection (Table 1). As a historical control, mortality rates for mice infected with a virulent variant, CB4-V, are included (Janeway and Travers, Immunobiology: The Immune System in Health and Disease. Third ed. London, New York: Current Biology Ltd./Garland Publishing Inc. 1997). Infectious CB4-P was cleared within one week of infection in BALB/c mice and within two weeks of infection in the immunodeficient.

TABLE I

Infection with CB4-P.

| Mouse Strain | Mortality (%) CB4-P | CB4-V |
|---|---|---|
| SJL | 0 | 0 |
| B10.T (6R) | 0 | 100 |
| B10.S (12R) | 0 | 0 |
| B10.Q | 0 | 55 |
| BALB/c | 0 | 67-100* |
| CD4 ko | 0 | 0 |
| IL-4 ko | 0 | 21-47* |
| γ-IFN ko | 0 | 21-100* |
| D011.10 | 0 | 0 |

Groups of 8-10 mice were infected with $10^4$ pfu of CB4-P;
*gender difference in survival.

While the CB4-P variant is attenuated, the virulent variant, CB4-V, induces a chronic pancreatitis which results in extensive destruction of the exocrine pancreas (Caggana et al., *J. Virol.* 67: 4797-803 (1993); Ramsingh et al., *J. Virol.* 71(11): 8690-7 (1997)). B10.T(6R) and male BALB/c mice succumb to infection within two weeks (Ramsingh et al., *Virus Res.* 14: 347-58 (1989); Janeway and Travers, Immunobiology: The Immune System in Health and Disease. Third ed. London, New York: Current Biology Ltd./Garland Publishing Inc. 1997). To determine if CB4-P can protect against infection with CB4-V, both strains of mice were tested by infection with CB4-P and two weeks later, with CB4-V. During the two-week follow-up after the second injection, all mice receiving CB4-P followed by CB4-V appeared healthy and had gained weight. Control mice infected with only CB4-P appeared healthy, but mice infected with CB4-V alone, by contrast, lost weight and became inactive. At the end of the two-week follow-up, mice were sacrificed and pancreatic tissues were processed for routine histology (FIG. 6). Pancreatic tissues from mice infected with CB4-V showed complete destruction of the acini with extensive calcification (FIG. 6C). A focal inflammatory infiltrate consisting primarily of mononuclear cells was evident. Pancreatic tissues from mice given CB4-P alone or both CB4-P and CB4-V appeared normal (FIGS. 6B,D).

Figure 13B:
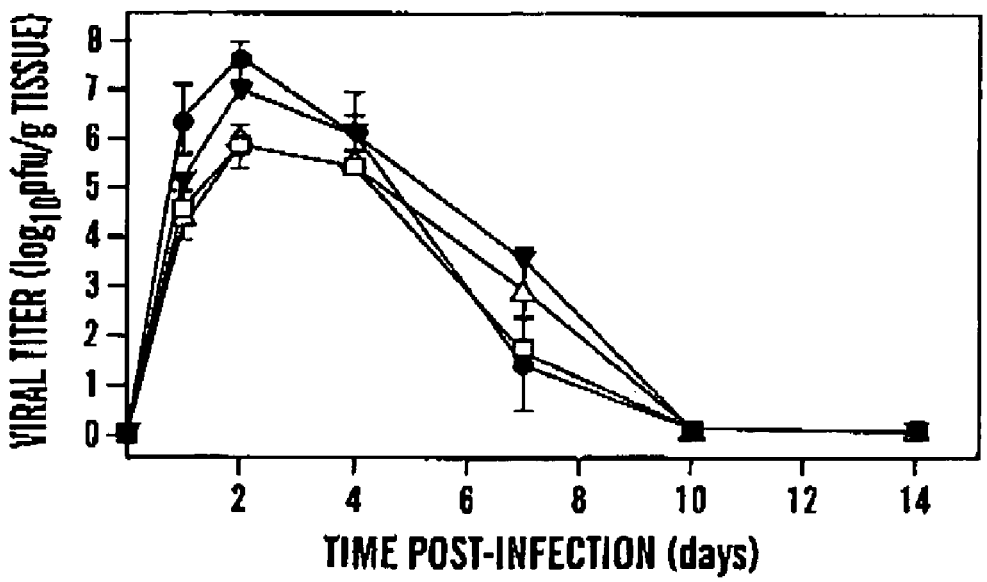

Recombinants containing 9 and 10 amino acids of HIV p24 sequences (SEQ ID NOS: 9-11, respectively in order of appearance) ($^{104}$IAGTTSTLQ$^{112}$, $^{148}$SSILDIRQG$^{156}$, $^{74}$NEEAAEWDRL$^{83}$) were constructed in a similar manner. The cloning strategy is outlined in FIG. 7. Oligonucleotides encoding nine (SEQ ID NOS: 12-13, respectively in order of appearance) ($^{104}$IAGTTSTLQ, $^{148}$SSILDIRQG) and ten amino acids (SEQ ID NO: 14 ($^{74}$NEEAAEWDRL) of HIV gag p24 sequences were inserted into the CB4-P cassette vector as previously described (Noben-Trauth et al., *Science:* 271987-90 (1996); Henderson et al., *J. Virol.* 66(4): 1856-65 (1992)). To retain two viral amino acids at positions 128 and 129 of VP1, and to maintain the correct reading frame, oligonucleotide sequences began with AGATG and ended with GAGG. Oligonucleotide sequences plus their complements were synthesized by the Molecular Genetics Core Facility. After the annealing reaction, oligonucleotide pairs were cloned, using standard methodologies, into the CB4-P cassette vector after digestion with StuI and NarI. Recombinants were screened initially by restriction enzyme analysis. Clones were identified based on the loss of the StuI site with retention of the NarI site. Clones were verified by DNA sequencing. To confirm the presence of HIV sequences within the viral recombinants, limited sequence analysis of viral genomic RNAs was carried out (Caggana et al., *J. Virol.* 67: 4797-803 (1993)). Briefly, LLC-MK2(D) cells were infected at a multiplicity of 0.2 pfu per cell. Total RNA was extracted 24 h later using Ultraspec RNA reagent (BioTecx). After reverse transcription using random primers, specific regions of the viral cDNA were amplified by PCR and sequenced. RNA from infected cells was sequenced at least twice.

RNA transcripts were then used to transfect LLC-MK2 (D) cells by electroporation (Noben-Trauth et al., *Science:* 271987-90 (1996)).

Briefly, 25-35 μg of RNA were added to $2\times10^6$ cells resuspended in calcium- and magnesium-free phosphate buffered saline. The cell suspension was subjected twice to an electric field of 0.8 kV/cm for 3 sec at room temperature using a GenePulser electroporator (Bio-Rad). The cell suspension was plated in two 60 mm tissue culture dishes containing DMEM and 5% fetal calf serum and incubated at 37° C. Virus was harvested when cells exhibited 80-100% cytopathic effects (CPE). Cells and media were collected and subjected to three cycles of freezing and thawing to release cell-associated virus. After a clarifying spin at 1400 g for 15 min at 4° C. to remove cellular debris, the supernate was collected and filtered through a 0.2 μM filter. Recombinant viruses were plaque-purified on LLC-MK2(D) cells. Large-scale stocks of plaque-purified recombinant viruses were prepared in LLC-MK2(D) cells.

Viable virus was obtained from all three of the CB4-P/HIV chimeric cDNAs. The chimeric viruses, CB4-P/HIV$9_{104}$, CB4-P/HIV$9_{148}$, and CB4-P/HIV$10_{74}$, retained their inserts after six passages in cell culture (FIG. 8). In addition, the three chimeric viruses were genetically stable after passage in vivo. The pathogenicity of the recombinants was assessed in male BALB/c mice since they succumb to infection with the virulent variant, CB4-V, but survive infection with CB4-P29. During the four week follow-up, mice infected with the chimeric viruses were well-groomed and appeared health indicating that the recombinants retained the avirulent phenotype of the parental CB4-P variant.

To elicit a CTL response, the foreign peptide need not be expressed as a structural component of CB4-P. In this strategy, foreign sequences are fused to the amino-terminus of the viral polyprotein and subsequently cleaved by a viral protease. The foreign sequences remain in the infected cell and are not incorporated into the virion.

A cassette vector that allowed insertion of foreign sequences at the amino terminus of the viral polyprotein was constructed (FIG. 7). The vector was made by inserting a sequence (18 bp) containing a unique restriction enzyme site, MluI, and a predicted recognition site for cleavage by the 3C protease, immediately after the initiator codon of the VP4 sequence. Briefly, the 18 bp sequence was inserted into a viral cDNA fragment by recombinant PCR. The amplified DNA was then used to replace the corresponding segment of a viral subclone containing the 5'UTR and the P I region of CB4-P within an XbaI-HindIII fragment (Caggana et al., *J. Virol.* 67: 4797-803 (1993)). Another subclone contained the P2, P3, and 3'UTR of CB4-P within a HindIII-SacI fragment (Caggana et al., *J. Virol.* 67: 4797-803 (1993)). The full-length cassette vector was constructed by ligating the XbaI-HindIII and the HindIII-SacI fragments simultaneously into pBSKS+ (Stratagene) as described previously (Caggana et al., *J. Virol.* 67: 4797-803 (1993)). Clones were screened initially by restriction enzyme analysis followed by DNA sequence analysis to confirm the presence of the 18 bp insert in the cDNA clone of the viral vector.

Virus, obtained from the cDNA clone of the vector, was passaged three times in cell culture and analyzed by sequencing the relevant region of the viral RNA. While the 18 base insert was retained in the virus vector, a point mutation was observed within the VP4 sequence at nucleotide position 768 (FIG. 7).

HIV gag p24 sequences were inserted into the CB4-P viral vector. To retain two viral amino acids at positions 128 and 129 of VP1, and to maintain the correct reading frame, sequences to be cloned began with AGATG and ended with GAGG. Sequences encoding amino acids 61-95, 61-122, and 61-180 of HIV gag p24 were amplified by PCR from a plasmid, HIV-gpt, which is replication-defective (Page et al., *J. Virol.* 64(11): 5270-6 (1990)). The HIV-gpt plasmid was kindly provided by Dr. Harold Burger (Wadsworth Center). To facilitate cloning of the p24 sequences, primers containing MluI recognition sites were used. The PCR products were cloned into the CB4-P polyprotein vector using standard methodologies. Clones were screened by restriction enzyme analysis and verified by DNA sequence analysis. Recombinant viruses were made as described above.

Since the size of the insert could affect viability and genetic stability, inserts of varying lengths were cloned into the viral vector. Inserts of 105, 186, and 360 nucleotides were cloned into the CB4-P vector. Viable viruses were obtained from all three constructs. The genetic stability of the recombinants was assessed initially by RT-PCR analysis after multiple passages in cell culture. After three passages, the CB4-P/HIV120 recombinant yielded at least two amplified products corresponding to retention of the 360 bp insert and loss of the entire insert. In contrast, after six passages, both CB4-P/HIV35 and CB4-P/HIV62 yielded single amplified products corresponding to insert sizes of 105 and 186 base pairs, respectively. The amplified products were characterized further by DNA sequencing. The CB4-P/HIV35 and CB4-P/HIV62 recombinants contained 105 and 186 nucleotides, respectively, of the p24 sequence (FIG. 9). Again, point mutations were observed at the same site, within the VP4 sequence of both recombinants. Like the virus vector, CB4-P/HIV62 contained an alanine residue at position two of VP4 while CB4-P/HIV35 contained a serine residue at the same position. Both recombinants were genetically stable after passage in vivo. The pathogenicity of the recombinants was assessed in male BALB/c mice. Mice survived infection with CB4-P/HIV35 and CB4-P/HIV62 and appeared healthy and gained weight.

To determine if cells infected with CB4-P/HIV35 and CB4-P/HIV62 were able to express and correctly process viral and foreign polypeptides, cell lysates were analyzed by immunoprecipitation. Cells were infected for five hours, labeled with [$^{35}$S] methionine, and proteins were immunoprecipitated with an anti-coxsackievirus or anti-gag p24 antibody. Briefly, LLC-MK2(D) cells grown in 60 mm plates were infected with virus (m.o.i.=5) and incubated for 5 h at 37° C. Cells were washed twice with PBS and incubated with cysteine/methionine-free D-MEM plus 5% fetal calf serum for 30 min at 37° C. [35S] methionine (50 µCi/ml; Amersham) was added to the cells. After 1 hour at 37° C., cells were washed twice with PBS and lysed in 0.5 ml of NP-40 lysis buffer (1% Nonidet P-40, 50 mM Tris-HCl, pH 7.6, 150 mM NaCl, 2 mM EDTA, 1 mM phenylmethylsulfonyl fluoride, 1 µM leupeptin, 1 µM pepstatin A, 2 µg/ml aprotinin). Cell lysates were clarified by centrifugation at 100,000 g for 1 h at 4° C.

Immunoprecipitations were carried out by incubating aliquots (100 µl) of cell lysates with various antibodies for 1 hour at 4° C. on a rocking platform. Normal horse serum and horse anti-CB4 polyclonal antibody (ATCC) were used at final concentrations of 1:300. Normal mouse serum and mouse anti-gag p24 monoclonal antibody (NEN Life Science Products, Inc.) were used at final concentrations of 1:500. Protein A-sepharose beads (Amersham) were added and samples were incubated at 4° C. for 30 minutes. Beads were washed four times with the NP-40 lysis buffer, resuspended in SDS-loading buffer, and run on an SDS-10% polyacrylamide gel.

Both CB4-P/HIV35 and CB4-P/HIV62 were able to produce and process viral capsid proteins in a manner similar to that observed for CB4-P (FIG. 10). However, the recombinants produced larger versions of the P1 capsid precursor and VP0 (lanes D,E), both of which contained gag p24 sequences (lanes H,I). A 70 kD protein was detected in lysates immunopreciptated with the anti-coxsackievirus antibody (lanes C,D,E). The molecular size of this protein suggests that it is an incompletely processed P1 recursor containing VP0 and VP3. Since the 70 kD protein was not detected by the anti-gag p24 antibody, this suggests that the gag p24 sequences were already cleaved. Both recombinants were also able to process the larger VP0 to produce a wild-type VP0 (lanes C,D,E) and presumably the gag p24 sequence, which was too small to be detected on these gels. Expression of the VP1 and VP3 capsid proteins of the recombinants appeared similar to that observed for CB4-P.

CB4-P/ova10 was shown to elicit a T helper cell response in mice previously infected with CB4-P. BALB/c mice, infected with $10^4$ pfu of CB4-P, cleared infectious virus and generated an anti-viral IgG response within one week of infection. For the double infections, BALB/c mice were first infected with $10^4$ pfu of CB4-P and then, two weeks later, were injected with $10^5$ pfu of the CB4-P/ova10 recombinant.

A proliferation assay was used to monitor the CD4+ T cell response to ovalbumin sequences in infected mice. To determine if the test recombinant, CB4-P/ova10, could elicit a T cell response in mice previously infected with CB4-P, BALB/c mice were injected intraperitoneally with $10^4$ pfu of CB4-P and then, two weeks later, with $10^5$ pfu of the recombinant. Spleens were harvested two weeks later and CD4+ T cells were purified. The purification protocol yielded a CD4+ T cell preparation that was 50-75% pure. Antigen presenting cells (APC), consisting primarily of B cells and macrophages, were purified from the spleens of uninfected BALB/c mice by negative selection (Coligan et al., Current Protocols in Immunology. New York: John Wiley & Sons, 1996). To prevent proliferation, the APC were treated with mitomycin C (25 µg/ml) for 20 min at 37°. The CD4+ T cells ($2\times10^5$) and APC ($2\times10^5$) were cultured in the presence of peptide (0-5 µg/well) or $5\times10^4$ pfu of heat-inactivated virus, in 96-well round bottom plates (Corning). (Peptides were synthesized by the Peptide Synthesis Core Facility using an Applied Biosystems 431A or 432A peptide synthesizer). After 4 days, cells were pulsed with 1 µCi of [$^3$H] methylthymidine (5 Ci/mmol) per well for 17 hours. Cells were harvested and lysed using an automatic cell harvester (Tomtec Cell Harvester 96). [$^3$H] thymidine incorporation was used as the indicator of CD4+ T cell activation. CD4+ T cells from the spleens of the doubly-infected mice proliferated in response to ovalbumin sequences, but not to an unrelated peptide (FIG. 11). T cells from uninfected mice or mice infected with only the CB4-P parental strain did not proliferate in response to the ovalbumin sequences.

EXAMPLE 3

Recombinants Retain Characteristics of Parental CB4-P Variant.

In this Example, the recombinants are shown to retain the biological and physical characteristics of the parental CB4-P variant.

Three recombinants were generated which express nine (CB4-P/HIV$9_{104}$, CB4-P/HIV$9_{148}$) and ten amino acids—(CB4-P/HIV$10_{74}$) of gag p24 as structural peptides, while two recombinants expressed thirty-five (CB4-P/HIV35) and sixty-two (CB4-P/HIV62) amino acids as non-structural sequences (Halim et al., *AIDS Research and Human Retroviruses* 16(15): 1551-1558 (2000)), as described in Example 2.

The thermal stability of the coxsackie/HIV recombinants (CB4-P/HIV35, CB4-P/HIV62, CB4-P/HIV91) was assessed by heat inactivation at 44° C. At 44° C., the parental CB4-P variant was more thermostable than a virulent variant, CB4-V. Both CB4-P/HIV35 and CB4-P/HIV62 retained the thermostable phenotype of the parental CB4-P variant while the CB4-P/HIV$9_{104}$ recombinant was inactivated more rapidly than CB4-P, but less rapidly than CB4-V (FIG. 12).

To determine if the insertion of foreign sequences into CB4-P affected replication, the growth kinetics of the recombinants were analyzed in cell culture and in mice. The kinetics of replication of CB4-P/HIV$9_{104}$ were similar to that of CB4-P under single step conditions (FIG. 13A). The kinetics of replication for CB4-P/HIV35 and CB4-P/HIV62 were also similar to that of CB4-P, but overall replication was less than that of the parental virus (FIG. 13A). The CB4-P/HIV35 recombinant replicated less well than the CB4-P/HIV62 recombinant. Replication of CB4-P/HIV35 was 10-to-100-fold less than that of CB4-P. Replication of CB4-P/HIV62 was 5-to-10-fold less than that of CB4-P.

Previous studies have shown that the pancreas is a major site of replication for CB4-P, which induces a mild, transient pancreatitis (Caggana et al., *J. Virol.* 67: 4797-803 (1993); Ramsingh et al., *J. Virol.* 71(11): 8690-7 (1997)). Viral replication in the pancreatic tissues of mice infected with the recombinants was assessed. The kinetics of replication for the three recombinants were similar to that of CB4-P. Viral titers peaked two days after infection and infectious virus was cleared by ten days after infection (FIG. 13B). As was observed in cell culture, overall replication of CB4-P/HIV9$_{104}$ in the pancreas was similar to that of CB4-P, while replication of CB4-P/HIV35 and CB4-P/HIV62 was lower than that of CB4-P. Early in infection both CB4-P/HIV35 and CB4-P/HIV62 replicated less well than CB4-P. During the first two days of infection, viral titers were 100-fold less in CB4-P/HIV35- and CB4-P/HIV62-infected tissues than in CB4-P-infected tissues. Titers of the recombinants, at four and seven days after infection, were similar to that of CB4-P.

Figure 14A:
Figure 14B:
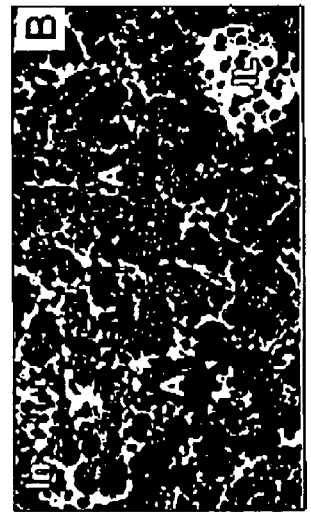
Figure 14C:
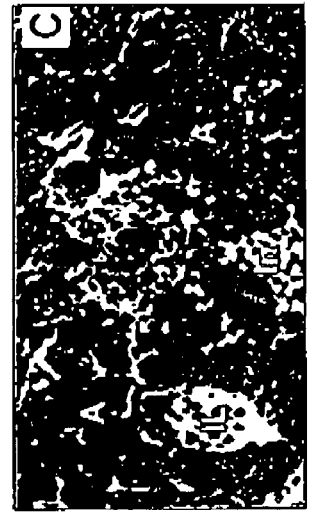
Figure 14D:
Figure 14E:
Figure 14F:

To determine if decreased viral replication correlated with less tissue injury, pancreatic damage during infection with either CB4-P/HIV35 or CB4-P/HIV62 was assessed by routine histology and compared to that induced by the parental CB4-P variant. As has been reported, infection with CB4-P results in a mild, transient inflammation of the exocrine pancreas (pancreatitis) while the endocrine pancreas, the islets of Langerhans, appears normal at the light microscopic level (Chapman et al., *Curr. Topics Microbiol. Immunol.*: 223227-58 (1997)). During infection with either recombinant, the extent of pancreatic tissue damage was less than that observed with the CB4-P variant (FIG. 14) and may reflect the overall lower viral titers in these tissues. A focal inflammatory infiltrate consisting primarily of mononuclear cells was evident from four to seven days after infection, yet the pancreatic architecture remained intact with minimal acinar cell necrosis (FIGS. 14A, B and C). By ten days after infection, when infectious virus was no longer present, the inflammatory response had subsided and the pancreatic architecture appeared normal (FIGS. 14D, E and F). Decreased viral replication correlated with less overall tissue damage. The data suggest that CB4-P/HIV35 and CB4-P/HIV62 are even less pathogenic than the avirulent CB4-P.

The results show that insertion of foreign sequences within the genome of CB4-P does not alter the physical stability of the recombinants. In addition, expression of a short peptide within the VP1 capsid does not alter the ability of the recombinant to replicate in cell culture or in mice. However, expression of longer sequences at the amino-terminus of the polyprotein results in decreased replication both in vitro and in vivo and correlates with diminished pathogenicity. The CB4-P/HIV recombinants retain the biological and physical properties of the attenuated CB4-P variant, which appears uniquely suited as a viral vector for a therapeutic HIV vaccine. Ongoing studies are focused on the immunogenicity of the recombinants. Should the CB4-P/HIV recombinants be able to elicit HIV-specific CD4+ T helper and CTL responses, a possible therapeutic vaccine strategy is a "cocktail" of recombinants expressing gag p24 sequences as structural and non-structural components.

Having thus described in detail preferred embodiments of the present invention, it is to be understood that the invention defined by the appended claims is not to be limited to particular details set forth in the above description as many apparent variations thereof are possible without departing from the spirit or scope of the present invention.

SEQUENCE LISTING

<160> NUMBER OF SEQ ID NOS: 32

<210> SEQ ID NO 1
<211> LENGTH: 16
<212> TYPE: PRT
<213> ORGANISM: Unknown Organism
<220> FEATURE:
<223> OTHER INFORMATION: Description of Unknown Organism: Peptide of the
      ryanodine receptor (RyR)

<400> SEQUENCE: 1

Arg Ala Glu Asn Glu Lys Asp Ala Thr Thr Glu Lys Asn Lys Lys Arg
 1               5                  10                  15

<210> SEQ ID NO 2
<211> LENGTH: 14
<212> TYPE: PRT
<213> ORGANISM: Unknown Organism
<220> FEATURE:
<223> OTHER INFORMATION: Description of Unknown Organism: Chimeric
      ova/virus peptide

<400> SEQUENCE: 2

Glu Met Ile Ser Gln Ala Val His Ala Ala His Ala Glu Ala
 1               5                  10

<210> SEQ ID NO 3
<211> LENGTH: 17
<212> TYPE: PRT
<213> ORGANISM: Unknown Organism
<220> FEATURE:
<223> OTHER INFORMATION: Description of Unknown Organism: OVA 323-339

```
<400> SEQUENCE: 3

Ile Ser Gln Ala Val His Ala Ala His Ala Glu Ile Asn Glu Ala Gly
  1               5                  10                  15
Arg

<210> SEQ ID NO 4
<211> LENGTH: 6
<212> TYPE: PRT
<213> ORGANISM: Coxsackievirus

<400> SEQUENCE: 4

Ile Ser Gln Ala Val His
  1               5

<210> SEQ ID NO 5
<211> LENGTH: 10
<212> TYPE: PRT
<213> ORGANISM: Coxsackievirus

<400> SEQUENCE: 5

Ile Ser Gln Ala Val His Ala Ala His Ala
  1               5                  10

<210> SEQ ID NO 6
<211> LENGTH: 14
<212> TYPE: PRT
<213> ORGANISM: Coxsackievirus

<400> SEQUENCE: 6

Ile Ser Gln Ala Val His Ala Ala His Ala Glu Ile Asn Glu
  1               5                  10

<210> SEQ ID NO 7
<211> LENGTH: 16
<212> TYPE: PRT
<213> ORGANISM: Coxsackievirus

<400> SEQUENCE: 7

Ile Ser Gln Ala Val His Ala Ala His Ala Glu Ile Asn Glu Ala Gly
  1               5                  10                  15

<210> SEQ ID NO 8
<211> LENGTH: 6
<212> TYPE: PRT
<213> ORGANISM: Coxsackievirus

<400> SEQUENCE: 8

Val His Ala Ala His Ala
  1               5

<210> SEQ ID NO 9
<211> LENGTH: 9
<212> TYPE: PRT
<213> ORGANISM: Human immunodeficiency virus

<400> SEQUENCE: 9

Ile Ala Gly Thr Thr Ser Thr Leu Gln
  1               5

<210> SEQ ID NO 10
<211> LENGTH: 9
<212> TYPE: PRT
<213> ORGANISM: Human immunodeficiency virus
```

```
<400> SEQUENCE: 10

Ser Ser Ile Leu Asp Ile Arg Gln Gly
 1               5

<210> SEQ ID NO 11
<211> LENGTH: 10
<212> TYPE: PRT
<213> ORGANISM: Human immunodeficiency virus

<400> SEQUENCE: 11

Asn Glu Glu Ala Ala Glu Trp Asp Arg Leu
 1               5                  10

<210> SEQ ID NO 12
<211> LENGTH: 9
<212> TYPE: PRT
<213> ORGANISM: Human immunodeficiency virus

<400> SEQUENCE: 12

Ile Ala Gly Thr Thr Ser Thr Leu Gln
 1               5

<210> SEQ ID NO 13
<211> LENGTH: 9
<212> TYPE: PRT
<213> ORGANISM: Human immunodeficiency virus

<400> SEQUENCE: 13

Ser Ser Ile Leu Asp Ile Arg Gln Gly
 1               5

<210> SEQ ID NO 14
<211> LENGTH: 10
<212> TYPE: PRT
<213> ORGANISM: Human immunodeficiency virus

<400> SEQUENCE: 14

Asn Glu Glu Ala Ala Glu Trp Asp Arg Leu
 1               5                  10

<210> SEQ ID NO 15
<211> LENGTH: 42
<212> TYPE: DNA
<213> ORGANISM: Coxsackievirus
<220> FEATURE:
<221> NAME/KEY: CDS
<222> LOCATION: (1)..(42)

<400> SEQUENCE: 15 cag gag atg tcc acc gcc act aac tca gat gtt cca gtg cag        42
Gln Glu Met Ser Thr Ala Thr Asn Ser Asp Val Pro Val Gln
 1               5                  10

<210> SEQ ID NO 16
<211> LENGTH: 14
<212> TYPE: PRT
<213> ORGANISM: Coxsackievirus

<400> SEQUENCE: 16

Gln Glu Met Ser Thr Ala Thr Asn Ser Asp Val Pro Val Gln
 1               5                  10

<210> SEQ ID NO 17
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      DNA vector
<220> FEATURE:
<221> NAME/KEY: CDS
<222> LOCATION: (1)..(42)

<400> SEQUENCE: 17 cag gcc ttg tcc acc gcc act aac tca gag gcg cca gtg cag          42
Gln Ala Leu Ser Thr Ala Thr Asn Ser Glu Ala Pro Val Gln
 1               5                  10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ala Leu Ser Thr Ala Thr Asn Ser Glu Ala Pro Val Gln
 1               5                  10

<210> SEQ ID NO 19
<211> LENGTH: 54
<212> TYPE: DNA
<213> ORGANISM: Coxsackievirus
<220> FEATURE:
<221> NAME/KEY: CDS
<222> LOCATION: (1)..(54)

<400> SEQUENCE: 19 cag gag atg ata tct caa gct gtc cat gca gca cat gca gag gcg cca     48
Gln Glu Met Ile Ser Gln Ala Val His Ala Ala His Ala Glu Ala Pro
 1               5                  10                  15 gtg cag                                                              54
Val Gln

<210> SEQ ID NO 20
<211> LENGTH: 18
<212> TYPE: PRT
<213> ORGANISM: Coxsackievirus

<400> SEQUENCE: 20

Gln Glu Met Ile Ser Gln Ala Val His Ala Ala His Ala Glu Ala Pro
 1               5                  10                  15

Val Gln

<210> SEQ ID NO 21
<211> LENGTH: 19
<212> TYPE: PRT
<213> ORGANISM: Coxsackievirus

<400> SEQUENCE: 21

Glu Met Ile Ser Gln Ala Val His Ala Ala His Ala Glu Ala Pro Val
 1               5                  10                  15

Gln Thr His

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
```

```
              DNA vector
<220> FEATURE:
<221> NAME/KEY: CDS
<222> LOCATION: (1)..(33)

<400> SEQUENCE: 22 atg acg cgt gct cta ttc caa gga aca cag gtg                          33
Met Thr Arg Ala Leu Phe Gln Gly Thr Gln Val
 1               5                  10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Thr Arg Ala Leu Phe Gln Gly Thr Gln Val
 1               5                  10

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA vector
<220> FEATURE:
<221> NAME/KEY: CDS
<222> LOCATION: (1)..(33)

<400> SEQUENCE: 24 atg acg cgt gct cta ttc caa gga gca cag gtg                          33
Met Thr Arg Ala Leu Phe Gln Gly Ala Gln Val
 1               5                  10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Thr Arg Ala Leu Phe Gln Gly Ala Gln Val
 1               5                  10

<210> SEQ ID NO 26
<211> LENGTH: 54
<212> TYPE: DNA
<213> ORGANISM: Artificial Sequence
<220> FEATURE:
<223> OTHER INFORMATION: Description of Artificial Sequence: Chimeric
      coxsackievirus containing HIV

<400> SEQUENCE: 26
caggagatga atgaggaagc tgcagaatgg gatagactag aggcgccagt gcag          54

<210> SEQ ID NO 27
<211> LENGTH: 51
<212> TYPE: DNA
<213> ORGANISM: Artificial Sequence
<220> FEATURE:
<223> OTHER INFORMATION: Description of Artificial Sequence: Chimeric
      coxsackievirus containing HIV
```

-continued

```
<400> SEQUENCE: 27
caggagatga tagcaggaac tactagtacc cttcaggagg cgccagtgca g          51

<210> SEQ ID NO 28
<211> LENGTH: 51
<212> TYPE: DNA
<213> ORGANISM: Artificial Sequence
<220> FEATURE:
<223> OTHER INFORMATION: Description of Artificial Sequence: Chimeric
      coxsackievirus containing HIV

<400> SEQUENCE: 28
caggagatga gcagcattct ggacataaga caaggagagg cgccagtgca g          51

<210> SEQ ID NO 29
<211> LENGTH: 239
<212> TYPE: DNA
<213> ORGANISM: Artificial Sequence
<220> FEATURE:
<223> OTHER INFORMATION: Description of Artificial Sequence: Chimeric
      coxsackievirus containing HIV
<220> FEATURE:
<221> NAME/KEY: CDS
<222> LOCATION: (10)..(237)

<400> SEQUENCE: 29 tacgataaa atg acg cgt gga cat caa gca gcc atg caa atg tta aaa gag     51
          Met Thr Arg Gly His Gln Ala Ala Met Gln Met Leu Lys Glu
            1               5                  10 acc atc aat gag gaa gct gca gaa tgg gat aga gtg cat cca gtg cat       99
Thr Ile Asn Glu Glu Ala Ala Glu Trp Asp Arg Val His Pro Val His
 15                  20                  25                  30 gca ggg cct att gca cca ggc cag atg aga gaa cca agg gga agt gac      147
Ala Gly Pro Ile Ala Pro Gly Gln Met Arg Glu Pro Arg Gly Ser Asp
                 35                  40                  45 ata gca gga act act agt acc ctt cag gaa caa ata gga tgg atg aca      195
Ile Ala Gly Thr Thr Ser Thr Leu Gln Glu Gln Ile Gly Trp Met Thr
             50                  55                  60 aat aat cca acg cgt gct cta ttc caa gga gca cag gtg tca ac          239
Asn Asn Pro Thr Arg Ala Leu Phe Gln Gly Ala Gln Val Ser Thr
 65                  70                  75

<210> SEQ ID NO 30
<211> LENGTH: 77
<212> TYPE: PRT
<213> ORGANISM: Artificial Sequence
<220> FEATURE:
<223> OTHER INFORMATION: Description of Artificial Sequence: Chimeric
      coxsackievirus containing HIV

<400> SEQUENCE: 30

Met Thr Arg Gly His Gln Ala Ala Met Gln Met Leu Lys Glu Thr Ile
  1               5                  10                  15

Asn Glu Glu Ala Ala Glu Trp Asp Arg Val His Pro Val His Ala Gly
                 20                  25                  30

Pro Ile Ala Pro Gly Gln Met Arg Glu Pro Arg Gly Ser Asp Ile Ala
             35                  40                  45

Gly Thr Thr Ser Thr Leu Gln Glu Gln Ile Gly Trp Met Thr Asn Asn
         50                  55                  60

Pro Thr Arg Ala Leu Phe Gln Gly Ala Gln Val Ser Thr
 65                  70                  75

<210> SEQ ID NO 31
```

```
<211> LENGTH: 158
<212> TYPE: DNA
<213> ORGANISM: Artificial Sequence
<220> FEATURE:
<223> OTHER INFORMATION: Description of Artificial Sequence: Chimeric
      coxsackievirus containing HIV
<220> FEATURE:
<221> NAME/KEY: CDS
<222> LOCATION: (10)..(156)

<400> SEQUENCE: 31 tacgataaa atg acg cgt gga cat caa gca gcc atg caa atg tta aaa gag       51
          Met Thr Arg Gly His Gln Ala Ala Met Gln Met Leu Lys Glu
            1               5                  10 acc atc aat gag gaa gct gca gaa tgg gat aga gtg cat cca gtg cat         99
Thr Ile Asn Glu Glu Ala Ala Glu Trp Asp Arg Val His Pro Val His
 15              20                  25                  30 gca ggg cct att gca cca ggc cag acg cgt gct cta ttc caa gga tca        147
Ala Gly Pro Ile Ala Pro Gly Gln Thr Arg Ala Leu Phe Gln Gly Ser
                 35                  40                  45 cag gtg tca ac                                                         158
Gln Val Ser Thr <210> SEQ ID NO 32
<211> LENGTH: 50
<212> TYPE: PRT
<213> ORGANISM: Artificial Sequence
<220> FEATURE:
<223> OTHER INFORMATION: Description of Artificial Sequence: Chimeric
      coxsackievirus containing HIV

<400> SEQUENCE: 32

Met Thr Arg Gly His Gln Ala Ala Met Gln Met Leu Lys Glu Thr Ile
  1               5                  10                  15

Asn Glu Glu Ala Ala Glu Trp Asp Arg Val His Pro Val His Ala Gly
                 20                  25                  30

Pro Ile Ala Pro Gly Gln Thr Arg Ala Leu Phe Gln Gly Ser Gln Val
             35                  40                  45

Ser Thr
 50
```

The invention claimed is:

1. A recombinant attenuated coxsackievirus B4 virion which is engineered to contain a heterologous non-coxsackievirus nucleic acid inserted within the P1 region of the open reading frame of its genome which inserted nucleic acid encodes a non-coxsackievirus heterologous polypeptide which is fused to a capsid protein of the virion.

2. The recombinant virion of claim 1 wherein the heterologous polypeptide is situated within an immunogenic region of the viral capsid protein.

3. The recombinant virion of claim 2 wherein the heterologous nucleic acid is expressed as an internal fusion of VP1.

4. The recombinant virion of claim 2 wherein the viral capsid protein is VP1.

5. The recombinant virion of claim 4 wherein the immunogenic region of VP1 comprises a B-cell epitope, a T-cell epitope, or both a B cell epitope and a T cell epitope.

6. The recombinant virion of claim 4 wherein the heterologous polypeptide is situated within VP1 at a position which corresponds to the DE loop.

7. The recombinant virion of claim 6 wherein the heterologous nucleic acid is directly downstream of codon 129 of VP1 coding sequences.

8. The recombinant virion of claim 7 wherein the nucleic acid sequence corresponding to VP1 codons 130-135 of wild type CB4 is deleted.

9. The recombinant virion of claim 1 wherein the heterologous nucleic acid is inserted in-frame and directly upstream of sequences which encode VP4, or is directly 3' from the AUG codon beginning at nucleotide 744 of the CB4 RNA genome that encodes the N-terminal Met of native viral polyprotein.

10. The recombinant virion of claim 9 wherein the heterologous polypeptide is expressed as an amino-terminal fusion of the viral polyprotein.

11. The recombinant virion of claim 10 wherein the amino-terminal fusion is susceptible to cleavage from the viral polyprotein by a viral protease.

12. The recombinant virion of claim 10 wherein the length of inserted heterologous nucleic acid is from about 60 to about 360 nucleotides.

13. A nucleic acid comprising the complete genome of a recombinant attenuated coxsackievirus B4 virion which is engineered to contain a heterologous non-coxsackievirus nucleic acid insert which is inserted within the P1 region of the open reading frame of its genome, wherein the insert encodes a non-coxsackievirus heterologous polypeptide which in the virion is fused to a capsid protein.

14. The nucleic acid of claim 13 which is an infectious cDNA of the CB4 genome.

15. The nucleic acid of claim 13 which is an infectious RNA of the CB4 genome.

16. The nucleic acid of claim 13 wherein the insert is in the coding region of VP1.

17. The nucleic acid of claim 16 wherein the insert is in sequences which encode the DE loop of VP1.

18. The nucleic acid of claim 17 wherein the insert is directly downstream of codon 129 of the VP1 coding sequences.

19. The nucleic acid of claim 18 wherein the nucleic acid sequence corresponding to VP1 codons 130-135 of wild type CB4 is deleted.

20. The nucleic acid of claim 13 wherein the insert is in-frame and directly upstream of sequences which encode VP4, or is directly 3' from the AUG codon, at nucleotide positions 744-746 of the CB4 RNA genome, that encodes the N-terminal Met of native viral polyprotein.

21. The nucleic acid of claim 18 wherein the insert is from about 25 nucleotides to about 39 nucleotides in length.

22. The nucleic acid of claim 18 wherein the polypeptide is immunogenic when fused to the VP1 capsid protein.

23. The nucleic acid of claim 22 wherein the insert encodes a T cell epitope, a B cell epitope, or both a T cell epitope and a B cell epitope.

24. The nucleic acid of claim 22 wherein the insert encodes a viral polypeptide or a peptide epitope thereof.

25. The nucleic acid of claim 22 wherein the insert encodes a polypeptide or a peptide epitope of a bacterial pathogen.

26. The nucleic acid of claim 22 wherein the insert encodes an HIV polypeptide or a peptide epitope thereof.

27. The nucleic acid of claim 26 wherein the insert encodes HIV p24 or a peptide epitope thereof.

28. A method for inducing an immune response to a polypeptide in a subject, comprising administering the recombinant attenuated coxsackievirus B4 virion of claim 1 to the subject under conditions appropriate for infection by the virion.

29. The method of claim 28 wherein the recombinant attenuated coxsackievirus B4 virion is formulated with a physiologically acceptable carrier.

30. The method of claim 28 wherein the immune response comprises the generation of a cytotoxic T-cell response, a T helper cell response, a B cell response, or any combination thereof.

31. The method of claim 28 wherein the heterologous nucleic acid encodes a T-cell epitope.

32. A method for inducing an immune response to a polypeptide in a subject, comprising administering a recombinant attenuated CB4 virion comprising the nucleic acid of claim 23 to the subject under conditions appropriate for infection by the virion.

33. A method for inducing an immune response to a polypeptide in a subject, comprising administering the recombinant attenuated CB4 virion of claim 3 to the subject under conditions appropriate for infection by the virion.

34. A method for inducing an immune response to a polypeptide in a subject, comprising administering the recombinant attenuated CB4 virion of claim 10 to the subject under conditions appropriate for infection by the virion.

35. A method for inducing an immune response to a polypeptide in a subject, comprising administering the recombinant attenuated CB4 virion of claim 11 to the subject under conditions appropriate for infection by the virion.

36. A method for inducing an immune response to a bacterial polypeptide in a subject, comprising administering a recombinant attenuated CB4 virion comprising the heterologous nucleic acid of claim 25 to the subject under conditions appropriate for infection by the virion.

37. The method of claim 36 wherein the immune response prevents or inhibits progression of a disease in the subject caused by bacteria comprising the heterologous bacterial polypeptide.

38. A method for inducing an immune response to a viral polypeptide in a subject, comprising administering a recombinant attenuated CB4 virion comprising the nucleic acid of claim 24 to the subject under conditions appropriate for infection by the virion.

39. The method of claim 38 wherein the immune response prevents or inhibits progression of a disease in the subject caused by a virus comprising the heterologous viral polypeptide, wherein the heterologous viral polypeptide comprises a viral epitope.

40. The method of claim 38 wherein the viral polypeptide is an HIV polypeptide or a peptide epitope thereof.

41. The method of claim 40 wherein the HIV polypeptide is p24 or a peptide epitope thereof.

42. The method of claim 28 wherein the subject is a human.

43. The method of claim 28 wherein the subject is an animal.

44. The method of claim 28 wherein the subject is immunocompromised.

45. A method for delivering a polypeptide to a subject, comprising administering to the subject, under conditions appropriate for infection, a recombinant attenuated coxsackievirus B4 virion which is engineered to comprise a non-coxsackievirus heterologous nucleic acid insert that is inserted within the open reading frame of the CB4 genome, which insert encodes the polypeptide being delivered, which polypeptide is
  (i) a heterologous non-coxsackievirus polypeptide fused to a capsid protein of the virion,
  (ii) expressed as an amino-terminal fusion with CB4 viral polyprotein; and
  (iii) susceptible to cleavage by a viral protease that cleaves the heterologous polypeptide from the viral polyprotein,
thereby delivering the polypeptide.

46. A recombinant attenuated coxsackievirus B4 virion consisting of a coxsackievirus B4 genome and a non-coxsackievirus heterologous nucleic acid inserted within the P1 region of the open reading frame of the genome, which inserted nucleic acid encodes a heterologous polypeptide which is fused to a capsid protein of the vinon.

* * * * *